(12) United States Patent
Maihle et al.

(10) Patent No.: US 7,744,882 B2
(45) Date of Patent: Jun. 29, 2010

(54) SOLUBLE ERBB3 METHODS OF DETECTION AND ANTIBODIES

(75) Inventors: Nita J. Maihle, New Haven, CT (US); Hakjoo Lee, Pittsford, NY (US)

(73) Assignee: Tumor Biology Investment Group, Inc., Lexington, KY (US)

( * ) Notice: Subject to any disclaimer, the term of this patent is extended or adjusted under 35 U.S.C. 154(b) by 0 days.

(21) Appl. No.: 12/144,375

(22) Filed: Jun. 23, 2008

(65) Prior Publication Data
US 2008/0274115 A1 Nov. 6, 2008

Related U.S. Application Data

(63) Continuation-in-part of application No. 10/159,353, filed on May 31, 2002, now Pat. No. 7,390,632.

(60) Provisional application No. 60/294,824, filed on May 31, 2001.

(51) Int. Cl.
A61K 39/00 (2006.01)
C07K 1/00 (2006.01)
C07K 16/00 (2006.01)
G01N 33/53 (2006.01)

(52) U.S. Cl. .................. 424/139.1; 530/387.9; 435/7.1

(58) Field of Classification Search .................. None
See application file for complete search history.

(56) References Cited

U.S. PATENT DOCUMENTS

| 4,522,811 | A | 6/1985 | Eppstein et al. |
|---|---|---|---|
| 4,676,980 | A | 6/1987 | Segal et al. |
| 4,741,900 | A | 5/1988 | Alvarez et al. |
| 4,816,397 | A | 3/1989 | Boss et al. |
| 4,816,567 | A | 3/1989 | Cabilly et al. |
| 4,946,778 | A | 8/1990 | Ladner et al. |
| 5,183,884 | A | 2/1993 | Kraus |
| 5,225,539 | A | 7/1993 | Winter |
| 5,252,348 | A | 10/1993 | Schreier et al. |
| 5,258,498 | A | 11/1993 | Huston et al. |
| 5,264,618 | A | 11/1993 | Felgner et al. |
| 5,459,127 | A | 10/1995 | Felgner et al. |

(Continued)

FOREIGN PATENT DOCUMENTS

EP 125023 11/1984

(Continued)

OTHER PUBLICATIONS

Lee et al., Oncogene, 16: 3243-3252, 1998 (cited on Applicant's IDS of Oct. 24, 2008).*

(Continued)

*Primary Examiner*—Cherie M Woodward
(74) *Attorney, Agent, or Firm*—Cohen & Grigsby, P.C.

(57) ABSTRACT

Regulation of sErbB3 isoforms in methods of regulating heregulin activity or ErbB receptor activities is disclosed. Cancer therapeutics and methods of therapeutically treating cancer comprising sErbB3 are also disclosed. Detection of sErbB3 in biological samples for risk assessment and prevention, screening, diagnosis, prognosis, theragnosis, evaluation of responsiveness to treatment, and/or monitoring of disease progression, recurrence, or metastasis of a cancer is disclosed as well. In examples, sErbB3 nucleic acid sequences, polypeptides, molecular probes, and antibodies are useful agents for regulation, expression, detection, and cancer therapeutics related to sErbB3.

9 Claims, 8 Drawing Sheets

Soluble Forms of the ErbB3 Receptor

U.S. PATENT DOCUMENTS

| | | | |
|---|---|---|---|
| 5,545,806 A | 8/1996 | Lonberg et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,738,976 A | 4/1998 | Okinoshima et al. | |
| 5,766,625 A | 6/1998 | Schreier et al. | |
| 5,807,683 A | 9/1998 | Brenner | |
| 5,968,511 A * | 10/1999 | Akita et al. | 424/141.1 |

FOREIGN PATENT DOCUMENTS

| | | |
|---|---|---|
| EP | 171496 | 2/1986 |
| EP | 173494 | 3/1986 |
| EP | 184187 | 6/1986 |
| WO | 8601533 | 3/1986 |
| WO | 8702671 | 5/1987 |

OTHER PUBLICATIONS

Alimandi, M., et al., Cooperative Signaling of ErbB3 and ErbB2 in Neoplastic Transformation and Human Mammary Carcinomas, Oncogene (1995) 10: 1813-1821.

Alroy, I., et al., The ErbB Signaling Network in Embryogenesis and Oncogenesis: Signal Diversification Through Combinatorial Ligand-Receptor Interactions, FEBS Letters, (1997) 410: 83-86.

Basu, A., et al., Inhibition of Tyrosine Kinase Activity of the Epidermal Growth Factor (EGF) Receptor by a Truncated Receptor Form That Binds to EGF: Role for Interreceptor Interaction in Kinase Regulation, Molecular and Cellular Biology, (1989) 9(2): 671-677.

Callaghan, T., et al., A Complete Description of the EGF-Receptor Exon Structure: Implication in Oncogenic Activation and Domain Evolution. Oncogene (1993) 8: 2939-2948.

Carraway, K., et al., Neuregulins and Their Receptors, Current Opinion in Neurobiology (1995) 5: 606-612.

Corfas, G. et al., Aria, A Protein that Stimulates Acetylcholine Receptor Synthesis, Also Induces Tyrosine Phosphorylation of a 185kDa Muscle Transmembrane Protein, Proc. Natl. Acad. Sci. USA, (1993) 90: 624-1628.

Doherty, J., et al., The Her-2/Neu Receptor Tyrosine Kinase Gene Encodes a Secreted Autoinhibitor, Proc. Natl. Acad. Sci. USA, (1999) 96(19): 10869-10874.

Fitzpatrick, V., et al. Formation of a High Affinity Heregulin Binding Site Using the Soluble Extracellular Domains of ErbB2 with ErbB3 or ErbB4, FEBS Letters., (1998) 431: 102-106.

Flickinger, T., W., et al., An Alternatively Processed mRNA from the Avian c-erbB Gene Encodes a Soluble, Truncated Form of the Receptor That Can Block Ligand-Dependent Transformation, Molecular and Cellular Biology, Molecular and Cellular Biology, (1992), 12(2): 883-893.

Hijazi, M. M. et al., Heregulin Regulates the Actin Cytoskelton and Promotes Invasive Properties in Breast Cancer Cell Lines, International Journal of Oncology, (2000) 17: 629-41.

Holmes, W. E., et al., Identification of Heregulin, A Specific Activator of p185erbB2, Science (1992) 256: 1205-1210.

Katoh, M., et al., c-erbB3 Gene Encodes Secreted as well as Transmembrane Receptor Tyrosine Kinase, Biochemical and Biophysical Research Communications, (1993) 192(3): 1189-1197.

Krane, I. M., et al., NDF/Heregulin Induces Persistence of Terminal End Buds and Adenocarcinomas in the Mammary Glands of Transgenic Mice, Oncogene (1996) 12: 1781-1788.

Kraus, M. H., et al., Isolation and Characterization of ERBB3, A Third Member of the ERBB/Epidermal Growth Factor Receptor Family: Evidence for Overexpression in a Subset of Human Mammary Tumors, Proc. Natl. Acad. Sci. USA, (1989) 86: 9193-9197.

Lax, I, et al., Functional Analysis of the Ligand Binding Site of EGF-Receptor Utilizing Chimeric Chicken/Human Receptor Molecules, The EMBO Journal, (1989) 8(2): 421-427.

Lee, H., et al., Isolation and Characterization of Four Alternate c-erbB3 Transcripts Expressed in Ovarian Carcinoma-Derived Cell Lines and Normal Human Tissues, Oncogene, (1998) 3243-3252.

Lewis, G. D., et al., Growth Regulation of Human Breast and Ovarian Tumor Cells by Heregulin: Evidence for the Requirement of ErbB2 as a Critical Component in Mediating Heregulin Responsiveness, Cancer Research (1996) 56: 1457-1465.

Marchionni, M. A., et al., Glial Growth Factors are Alternatively Spliced erbB2 Ligands Expressed in the Nervous System, Nature (1993) 362: 312-318.

Meyer, D., et al., Multiple Essential Functions of Neuregulin in Development, Nature (1995) vol. 378: 386-390.

Peles, E, et al., Isolation of the Neu/HER-2 Stimulatory Ligand: A 44 kd Glycoprotein That Induces Differentiation of Mammary Tumor Cells, Cell (1992) 69: 205-16.

Plowman, G. D., et al. Ligand-Specific Activation of HER4/p180erbB4, A Fourth Member of the Epidermal Growth Factor Receptor Family, Proc. Natl. Acad. Sci USA (1993) 90: 1746-1750.

Plowman, G. D., et al., Molecular Cloning and Expression of an Additional Epidermal Growth Factor Receptor-Related Gene, Proc. Natl. Acad. Sci, USA (1990) 87: 4905-4909.

Ram T.G., et al., Blocking HER-2/HER-3 function with a Dominant Negative Form of HER-3 in Cells Stimulated by Heregulin and in Breast Cancer Cells with HER-2 Gene Amplification, Cell Growth & Differentiation, (2000) 11: 173-183.

Redemann, N., et al., Anti-Oncogenic Activity of Signalling-Defective Epidermal Growth Factor Receptor Mutants, Molecular and Cellular Biology (1992) 12(2): 491-498.

Robinson, D. et al., A Tyrosine Kinase Profile of Prostate Carcinoma, Proc. Natl. Acad. Sci. USA (1996) 93: 5958-5962.

Siegel, P. M., et al., Elevated Expression of Activated Forms of Neu/ErbB-2 and ErbB-3 are Involved in the Induction of Mammary Tumors in Transgenic Mice: Implications for Human Breast Cancer, The EMBO Journal (1999) 18(8): 2149-2164.

Singer, E., et al., Identification of a Heregulin Binding Site in HER3 Extracellular Domain, The Journal of Biological Chemistry, (2001) 276(47): 44266-74.

Sundaresan, S. et al., The Biology of Human Epidermal Growth Factor Receptor 2, Current Oncology Reports (1999) 1: 16-22.

Tsai, M. S., et al. Expression and Function of CYR61, An Angiogenic Factor, in Breast Cancer Cell Lines and Tumor Biopsies, Cancer Research (2000) 60: 5603-5607.

Vartanian, T., et al., Axonal Neuregulin Signals Cells of the Oligodendrocyte Lineage through Activation of HER4 and Schwann Cells through HER2 and HER3, The Journal of Cell Biology (1997) 137(1): 211-220.

Wen, D., et al., Neu Differentiation Factor: A Transmembrane Glycoprotein Containing an EGF Domain and an Immunoglobulin Homology Unit, Cell (1992) 69: 559-572.

Chen X. et al., An Immunological Approach Reveals Biological Differences Between the Two NDF/Heregulin Receptors, ErbB-3 and ErbB-4 J Biol. Chem. Mar. 29, 1996; 271(13) 7620-7629.

Tzahar, E. et al., ErbB-3 and ErbB-4 Function as the Respective Low and High Affinity Receptors of all Neu Differentiation Factor/Heregulin Isoforms, J Biol. Chem. (1994) 269(40): 25226-25233.

Slivkowski, M. et al., Coexpression of erbB2 and erbB3 Proteins Reconstitutes a High Affinity Receptor for Heregulin, J.Biol. Chem. (1994) 269(20): 14661-14665.

Strausberg, R. L., et al., Generation and Initial Analysis of More than 15,000 Full-Length Human and Mouse cDNA Sequences, PNAS USA (2002) 99(26): 16899-903.

Wells, J., Addivity of Mutational Effects in Proteins, Biochemistry (1990) 29(37): 8509-8517.

Bowie, J., et al., Deciphering the Message in Protein Sequences: Tolerance to Amino Acid Substitutions, Science (1990) 247: 1306-1310.

Lee, H. et al., A Naturally Occurring Secreted Human ErbB3 Receptor Isoform Inhibits Heregulin-Stimulated Activation of ErbB2, ErbB3 and ErbB4, Cancer Research (2001) 61: 4467-4473.

Sue, Hiwa Lin et al., Soluble ErbB3 Levels in Bone Marrow and Plasma of Men with Prostate Cancer, Clinical Cancer Research (2008) 14(12) 3729-3736.

Kwong, K.Y. et al., A Novel Splice Varian of HER2 with Increased Transformaton Activity, Molecular Carinogenesis 23: 62-68 (1998).

Baselga, Jose et al., Targeting Tyrosine Kinases in Cancer: The Second Wave, Science, 312: 1175 (2006).

Juntilla, T.T. et al., ErbB4 and its Isoforms Selective Regulation of Growth Factor Responses by Naturally Occurring Receptor Variants Trends, Cardiovasc Med 10: 304-310 (2000).

Saez, R. et al., p95HER-2 Predicts Worse Outcome in Patients with HER-3-Positive Breast Cancer, Clinical Cancer Research 12(2): 424 (2006).

Hume, C.R. et al., Erb Expression: The Mouse Inner ear and Maturation of the Mitogenic Response to Heregulin, JARO 04: 422-443 (2003).

Corfas, G. et al., A Protein that Stimulates Acetylcholine Receptor Synthesis, Also Induces Tyrosine Phosphorylation of a 185-kDa Muscle Transmembrane Protein, Celll 71 (5): 801-15 (1993).

Walters, D.K. et al., Atypical Expression of ErbB3 in Myeloma Cells: Cross-talk Between ErbB3 and the Interfereon-signaling complex, Oncogene 22 (23): 3598-607 (2003).

Cunningham, B. et al., High Resolution Epitope Mapping of gGH-Receptor Interaction by Alanine-Scanning Mutagenesis, Science 244: 1081-1085, 1989.

Adelman, J. et al., In Vitro Mutagenesis for Bacterial Production of the 20,000-Dalton Form of Human Pituitary Growth Hormone, DNA 2:183, 1983.

Hyrup, et al., Peptide Nucleic Acids (PNA): Synthesis Properties and Potential Applications, Bioorganic & Medicinal Chemistry 4:523, 1996.

Stein, C.A., Oligodeoxynucleotides as Inhibitors of Gene Expression, Cancer Res 48: 2659, 1988.

Van Der Krol, et al., Modulation of Eukaryotic Gene Expression by Complementary RNA or DNA Sequences, Bio Techniques 6:958, 1998.

Izant, J.G.et al. Inhibition of Thymidine Kinase Gene Expression by Anti-Sense RNA: A Molecular Approach to Genetic Analysis, Cell 36: 1007-1015, 1984.

Rosenberg, et al., Productions of Phenocopies by Kuppel Antisense RNA Injection into Dosophilla Embryos, Nature 313: 703-706 1985.

Curiel, D. et al., et al., Gene Transfer to Respiratory Epithelial Cells Via the Receptor-Mediated Endocytosis Pathway, Respir Cell Mol Biol 6: 247-52, 1992.

Felgner, et al., Lipofection: A Highly Efficient, Lipid Mediated DNA-Transfection Procedure, PNAS 84: 7413-7417, 1987.

Felgner, et al., Improved Cationic Lipid Formulations for In Vivo Gene Therapy, Annals NY Acad Sci: 772: 126-139, 1995.

Bousiff, et al., A Versatile Vector for Gene and Oligonucleotic Transfer into Cells in Culture and In Vivi: Polyethylenimine, PNAS 92: 7297-7301, 1995.

Kohler et al. Continuous Cultures of Fused Cells Secreting Antibody of Predefined Specificity, Nature 256: 495-497 1975.

Kozbor al., The Production of Monoclonal Antibodies from Human Lyphocytes, Immunology Today 4:72 1983.

Cole, et al., The EBV-Hybridoma Technique and Its Application to Human Lung Cancer, Monoclonal Antibodies & Cancer Therapy, Allan R. Liss, Inc. p. 77-96, 1985.

Bettler, M. et al., Escherichia coli Secretion of an Active Chimeric Antibody Fragmant, Science 240: 1041-1043, 1988.

Liu, et al., Chimeric Mouse-Human IgG! Antibody That Can Mediate Lysis of Cancer Cells, PNAS USA 84: 3439-3443, 1987.

Liu, et al., Production of A Mouse-Human Chimeric Monoclonal Antiboby to CD20 with Potent Fc-Dependent Biological Activity, Journal of Immunol 139: 3521-3526 1987.

Sun, et al., Chimeric Antibody with Human Constant Regions and Mouse Variable Regions Directed Against Carcinoma-Associated Antigen 17-1A, PNAS 84: 214-218 1987.

Nishimusa, et al., Recombinant Human-Mouse Chimeric Monoclonal Antibody Specific for Common Acute Lyphocytic Leukemia Antigen, Cancer Res. 47: 999-1005, 1987.

Wood, et al., The Synthesis and In Vivo Assembly of Functional Antibodies in Yeast, Nature 314: 446-449 1985.

Shaw, et al., Mouse/Human Chimeric Antibodies of a Tumor-Associated Antigen: Biologic Activity of the Four Human IgG Subclasses, J. Nat'l Cancer Inst. 80: 1553-1559, 1988.

Morrison, Transforming Provide Novel Chimeric Antibodies, Science 229: 1202-1207, 1985.

Oi, et al., Chimeric Antibodies, Bio Techniques 4:214, 1986.

Jones, et al., Replacing the Complementarity-Determining Regions in a Human Antibody with Those from a Mouse, Nature 321: 552 1986.

Verhoeyan, M. et al. Reshaping Human Antibodies: Grafting an Antilysozyme Activity, Science 239: 1534 1988.

Biedler, et al. Cloning and High Level Expression of Chimeric Antibody with Specificity for Human Carcinoembryonic Antigen, J. Immunol 141: 4053-4060 1988.

Neuberger, et al., Recombinant Antibodies Posessing Novel Effector Functions, Nature 312: 604-608 1984.

Takeda, et al., Construction of Chimaeric Processed Immunoglobulin Genes Containing Mouse Variable and Human Constant Region Sequences, Nature 314: 452-454 1985.

Lonberg N. et al., Human Antibodies from Transgenic Mice, Int. Dev. Ininunol 13: 65-93 1995.

Jespers, et al., Guiding the Selection of Human Antibodies form Phage Display Repertoires to a Single Epitope of an Antigen, Biotechnology, 12:899-903, 1994.

Ward, et al., Binding Activities of a Reprtoire of Single Immunoglulin Variable Diomains Secreted for Excherichia coli, Nature 334: 544-54, 1989.

Shu, et al., Secretion of a Single-Gene-Encoded immunoglobulin form Myeloma Cells, PNAS 90: 7995-7999 1993.

Skerra, et al., Assembly of a Functional Immunoglbulin Fv Fragment in Escherichia Coli, Science 240: 1038-1040, 1988.

Suresh, et al., Bispecific monoclonal Antibodies from Hybrid Hybridomas, Methods in Enzymology 121: 210, 1986.

Bird, Single-Chain Antigen-Binding Proteins, Science 242: 42342 1988.

Huston, et al., Protein Engineering of Antibody binding Sites: Recovery of Specific Activity in an Anti-Digoxin single-Chain Fv Analogue Produced in Escherichia coli PNAS, USA 85: 5879-5883, 1988.

Huston, et al., Protein Engineering of A Single-Chain Fv Analogs and fusion Proteins, Methods in Enzymology 203: 46-88 1991.

Kutmeier, et al., Assembly of Humanized Antibody Genes form Synthetic Oligonucleotides Using a Single-Round PCR, Bio Techniques 17: 242 1994.

Ruther, et al., Easy Identification of cDNA Clones, EMBO J 2: 1791, 1983.

Inouye et al., Up-Promoter Mutations in the Ipp Gene of Escherichia coli, Nucleic Acids Res 13: 3101-3109,1985.

Van Heeke et al., Expression of Human Asparagine Synthetase in Escherichia coli, J. Biol Chem 24: 5503-5509, 1989.

Proudfoot, N., Transcriptional Interference and Termination Between Duplicated a-Globin Gene Constructs Suggest a Novel Mechanism for Gene Regulation, Nature 322:52, 1986.

Kohler G., Immunoglobulin Chain Loss in Hybridoma Lines, PNAS 77:2197, 1980.

Arnon, et al. "Monoclonal Antibodies for Immunotargeting of Drugs in Cancer Therapy" in Monoclonal Antibodies & Cancer Therapy, Reisfield, et al. (eds) p. 243-56 (Alan R. Lisss, Inc. 1985).

Hellstorm, et al. "Antibodies for Drug Delivery" Controlled Drug Delivery (2nd ed) Robinson, et al. (eds) p. 623-53 (Marcel Dekker, Inc. 1987).

Thorpe, Antibody Carriers of Cytotoxic Agents in Cancer Therapy: A Review in Monoclonal Antibodies '84: Biological & Clinical Applications Pinchera, et al. (eds) pp. 475-506 (1985).

Baldwin et al., Analysis, Results & Future Prospective of the Therapeutic Use of Radiolabeled Antibody in Cancer Therapy in Monoclonal Antibodies for Cancer Detection & Therapy. 303-16 Academ. Press 1985).

Lam Anticancer Drugs Des 12:145 1997.

Tyle, P., "Iontophoretic Devices for Drug Delivery," Pharmaceutical Research 3(6): 318, 1986.

Sithanadam G. et al., The ErbB3 Receptor in Cancer and Cancer Gene Therapy, Cancer Gene Therapy 1-36 (2008).

Chen, N. et al., A Secreted Isoform of ErbB3 Promotes Osteonectin Expression in Bone and Enhances the Invasiveness of Prostate Cancer Cells, Cancer Research 67 (14): 6544-6548 (2007).

Vakar-Lopez, F. et al., Up-Regulation of MDA-BF-1, A Secreted Isoform of ErbB3, in Metastatic Prostate Cancer Cells and Activatied Osteoblasts in Bone Marrow, Journal of Pathology 2203: 688-695 (2004).

Breuleux, M., Role of Heregulin in Human Cancer, Cellular and Molecular Life Sciences, 64: 2358-2377 (2007).

Hemi, R. et al., Transactviation of ErbB3 by Tumor Necrosis Factor- and Anisomycin Leads to Impaired Insulin Signaling Through Serine/Threonin Phoshorylation of IRS Proteins, The Journal of Biological Chemistry, 277: 8961-8969 (2002).

Falls, DL et al. Aria, A Protein that Stimulates Acetylcholine receptor Synthesis, Is a Member of the New Ligand Family, Cell 72(5): 801-15 (1993).

UniPro database entry, Q9BUB7 HUMAN, Accession No. Q9BUB7, ://www.pir.uniprot.org/cgi-bin/upEntry?id=Q9BUB7_HUMAN, Sep. 20, 2006, 3 pages.

Maniatis, T. et al., Molecular Cloning: A Laboratory Manual, Chapters 1, 2, 3, 7, 12, Cold Spring Harbor Laboratory, 1982.

Ausubel, F. et al., Current Protocol in Molecular Biology, vol. 1, Chapters 1, 9, 11, 12, 1987.

Wallasch, C. et al., Heregulin-Dependent Regulation of HER2/neu Oncogenic Signaling by Heterodimerization With HER3, The EMBO Journal, vol. 14, No. 17, pp. 4267-4275, 1995.

* cited by examiner

SOLUBLE ERBB3 METHODS OF DETECTION AND ANTIBODIES

This application is a continuation-in-part of U.S. application Ser. No. 10/159,353 filed May 31, 2002, which claims priority to U.S. Provisional Application 60/294,824 filed May 31, 2001.

The disclosed invention was made with the support of a grant from the National Cancer Institute (CA85133). The United States Government has certain rights in the invention.

FIELD OF INVENTION

Embodiments of the present invention generally pertain to methods and therapeutics that relate to soluble ErbB3 proteins (sErbB3), such as p85-sErbB3, p45-sErbB3 and other isoforms of sErbB3. Embodiments of the present invention pertain to methods of treating cancer and cancer therapeutics comprising an sErbB3 or an sErbB3 agent regulating expression or activity of an sErbB3. Additional embodiments of the present invention pertain to sErbB3 regulation of heregulin or at least one ErbB receptor activity and treatment of associated conditions. Other embodiments relate to risk assessment and cancer prevention, screening, diagnosis, prognosis, theragnosis, monitoring of responsiveness to treatment, and monitoring of disease progression, recurrence, or metastasis of a cancer based on aberrant sErbB3 concentrations or localization in biological samples, for example serum or tissue.

BACKGROUND

The following background information is provided to assist the reader to understand the invention disclosed below and the environment in which it will typically be used. The terms used herein are not intended to be limited to any particular narrow interpretation unless clearly stated otherwise, either expressly or impliedly, in this document.

The heregulins (also called neuregulins, neu differentiation factor (NDF), acetylcholine receptor inducing activity (ARIA), and glial growth factors (GGFs)) are a family of growth factors that activate members of the ErbB/EGF receptor family (Holmes, Sliwkowski et al. 1992; Peles, Bacus et al. 1992; Wen, Peles et al. 1992; Falls, Rosen et al. 1993; Marchionni, Goodearl et al. 1993). Isoforms of heregulins, all of which arise from splice variants of a single gene, NRG-1 (neuregulin-1), have been cloned and classified into the α and β subgroups based on structural differences in their epidermal growth factor (EGF) like domains (Holmes, Sliwkowski et al. 1992).

ErbB-mediated signal transduction exerted by heregulins has been implicated in the regulation of diverse biological events including Schwann cell differentiation, neural regulation of skeletal muscle differentiation, heart development, and proliferation and differentiation of normal and malignant breast epithelial cells (Alroy and Yarden 1997; Sundaresan, Penuel et al. 1999). Research has shown that breast carcinoma cells respond to heregulin by activating signal transduction pathways that result in cellular proliferation, differentiation, as well as morphogenesis. Carcinoma cells expressing heregulin are typically hormone-independent and associated with the ability for metastasis in experimental studies.

ErbB3 is a transmembrane glycoprotein encoded by the c-erbB3 gene (Kraus, Issing et al. 1989; Plowman, Whitney et al. 1990). The ErbB3 receptor belongs to the ErbB family which is composed of four growth factor receptor tyrosine kinases, known as ErbB1/EGFR/HER1, ErbB2/Neu/HER2, ErbB4/HER4, as well as ErbB3/HER3. ErbB3 and ErbB4 are receptors for heregulins, whereas ErbB2 is a coreceptor (Carraway and Burden 1995). These receptors are structurally related and include three functional domains: an extracellular ligand-binding domain, a transmembrane domain, and a cytoplasmic tyrosine kinase domain (Plowman, Culouscou et al. 1993). The extracellular domain can be further divided into four subdomains (I-IV), including two cysteine-rich regions (II and IV) and two flanking regions (I and III). ErbB3 is unusual among these receptor tyrosine kinases in that its catalytic domain is defective. Despite its lack of intrinsic catalytic activity, ErbB3 is an important mediator of both heregulin and epidermal growth factor (EGF) responsiveness by way of its ability to heterodimerize with other ErbB family members, but especially with ErbB2. Heregulin binding induces ErbB3 to associate with other members of the ErbB family to form heterodimeric receptor complexes. ErbB3 then activates the kinase of its partner receptor which initiates a variety of c signaling cascades. ErbB3 also can relay information in response to diverse ligands, such as interferon and TNF-alpha, presumably through receptor cross-talk.

The ErbB3 receptor is important in regulating normal and aberrant cellular growth and differentiation, metastasis, and related pathologies. Transgenic mice that have been engineered to overexpress heregulin in mammary glands have been reported to exhibit persistent terminal end buds and, over time, to develop mammary adenocarcinomas (Krane and Leder 1996). ErbB3 expression studies on tumor tissues and on cancer cell lines show frequent co-expression of both ErbB2 and ErbB3 receptors (Alimandi, Heidaran et al. 1995; Meyer and Birchmeier 1995; Robinson, He et al. 1996; Siegel, Ryan et al. 1999). In addition, mammary tumors formed in transgenic mice that harbor an activated form of ErbB2 and metastasize to the lungs are associated with elevated amounts of tyrosine-phosphorylated ErbB2/Neu and ErbB3 (Siegel, Ryan et al. 1999). Many transformed cell lines used for experimental studies are either estrogen-dependent (MCF-7 and T47D, the low ErbB2 expressers) or estrogen-independent (SKBR3, high ErbB2 expressers). However, these cell lines do not exhibit metastatic phenotypes. When MCF-7 cells are transfected to overexpress ErbB2, MCF-7 cells gain an estrogen-independent phenotype, however, they never metastasize. On the other hand, MCF-7 cells that overexpress heregulin gain a metastatic phenotype, suggesting that the heregulins play an active role in metastasis (Hijazi, Thompson et al. 2000; Tsai, Hornby et al. 2000).

Five alternate ErbB3 transcripts arise from read-through of an intron and the use of alternative polyadenylation signals (Lee and Maihle 1998; Katoh, Yazali et al. 1993). Using 3'-RACE four novel c-erbB-3 cDNA clones of 1.6, 1.7, 2.1, and 2.3 kb from a human ovarian carcinoma-derived cell line have been isolated (Lee and Maihle 1998). p85-sErbB3 is encoded by a 2.1 kb alternate c-erbB3 transcript (cDNA clone R31F) that is translated into a 543 aa protein composed of subdomains I through III and the first third of subdomain IV of the ErbB3 extracellular domain, and a unique 24 amino acid carboxy-terminal sequence. p45-sErbB3 is encoded by a 1.7 kb alternate c-erbB3 transcript (cDNA clone R2F) that is translated into a 312 aa protein composed of subdomains I, II, and a portion of subdomain III of the extracellular domain of ErbB-3 followed by two unique glycine residues. p50-sErbB3 is encoded by a 1.6 kb alternate c-erbB3 transcript (cDNA clone R1F) that is translated into a 381 aa protein composed of subdomains I, II, and a portion of subdomain III of the extracellular domain of ErbB-3 followed by 30 unique amino acids. p75-sErbB3 is encoded by a 2.3 kb alternate c-erbB3 transcript (cDNA clone R35F) that is translated into a 515 aa protein composed of subdomains I through III, and has a unique 41 amino acid carboxy-terminal sequence (FIG. 1)(Lee and Maihle 1998).

A recombinant dominant-negative ErbB3 mutant with a deleted cytoplasmic domain but which retains its transmembrane domain can inhibit full-length ErbB2 and ErbB3 receptor phosphorylation and signal transduction (Ram, Schelling et al. 2000). In avian tissues, expression of a naturally occurring sEGFR/ErbB 1 inhibits TGFα dependent cellular transformation (Flickinger, Maihle et al. 1992). An aberrant soluble EGFR/sErbB1 secreted by the A431 human carcinoma cell line has been reported to inhibit the kinase activity of full-length EGFR in a ligand-independent manner (Basu, Raghunath et al. 1989). Similarly, herstatin, a naturally occurring soluble ErbB2 isoform which inhibits ErbB2 receptor phosphorylation and signaling, appears to function by blocking ErbB2 dimerization (Doherty, Bond et al. 1999). In no case do these soluble ErbB isoforms function as antagonists of ErbB receptor signaling through competitive, high affinity ligand binding.

Soluble ErbB3 proteins, for example p85-sErbB3 and p45-sErbB3, are unique among other naturally occurring soluble ErbB isoforms in that they bind specifically to heregulin with high affinity. Consequently, sErbB3 inhibits heregulin binding to cell surface ErbB receptors and heregulin-induced activation of the ErbB receptors and their downstream effectors. Thus sErbB3, such as p85-sErbB3 and p45-sErbB3, can be used as therapeutic reagents for heregulin-regulated malignancies such as mammary, prostate, ovary, and lung tumors. In addition, through receptor cross-talk, as well as through interactions with heterologous cell surface receptors, these soluble receptor isoforms may also be important for nonheregulin-associated conditions.

SUMMARY OF THE INVENTION

Embodiments of the present invention pertain to several novel isolated and purified nucleic acid sequences which encode soluble isoforms of ErbB3 (sErbB3). For example, embodiments of this aspect of the invention include nucleic acid sequences which specifically encode a soluble form of ErbB3 whose amino acid sequence comprises the sequence of SEQ ID NO: 2 or SEQ ID NO: 4. The related nucleic acid sequence embodiments comprise SEQ ID NO: 1 and SEQ ID NO: 3, respectively.

Various embodiments of the present invention relate to an sErbB3 agent for expression of sErbB3 or regulation of sErbB3 function or expression (either transcription or translation). Examples of an sErbB3 agent include without limitation a polypeptide, a nucleic acid sequence (RNA or DNA, sense or antisense), an sErbB3 antibody, an expression vector, a small molecule, or a polypeptide agonist or antagonist.

Various embodiments of the present invention pertain to methods for treating cancer comprising an sErbB3 agent. Other embodiments relate to sErbB3 agents as cancer therapeutics. Additional embodiments of the present invention relate to isoforms of sErbB3 that bind to heregulin (HRG) with high affinity and effectively block HRG binding to cell surface receptors. For example, p85-sErbB3 binding to HRG with high affinity substantially blocks HRG binding to cell surface receptors. Other embodiments of the present invention pertain to the use of an sErbB3 agent to regulate ErbB receptor signal transduction pathways and biological effects on cellular proliferation, differentiation, and metastasis. Embodiments of the present invention also pertain to the risk assessment and prevention, screening, diagnosis, prognosis, theragnosis, treatment, and evaluation of responsiveness to treatment, and monitoring of disease progression, recurrence, or metastasis of cancer cells using sErbB3 isoforms, such as p45-sErbB3 or p85-sErbB3.

Another embodiment of the present invention pertains to an expression vector, such as a plasmid or virus, containing an isolated cDNA encoding an sErbB3 isoform, such as p45-sErbB3 or p85-sErbB3, as well as a eukaryotic or prokaryotic cell containing the expression vector.

Embodiments of the present invention also pertain to a process for producing the p85-sErbB3 isoform and other sErbB3 isoforms, which comprises the steps of ligating the isolated cDNA into an expression vector capable of expressing the isolated cDNA in a suitable host; transforming the host with the expression vector; culturing the host under conditions suitable for expression of the isolated cDNA and production of the p85-sErbB3 protein or other sErbB3 isoforms, and isolating the protein from the host. The host cell may be a prokaryote or a eukaryote.

Additional embodiments of the present invention relate to molecular probes and antibody reagents specific for the unique region of p85-sErbB3 or other sErbB3 isoform epitopes. For example, polyclonal and monoclonal antibodies specific to p85-sErbB3 are generated using a unique C-terminal sequence of the p85-sErbB3 as an antigen. The affinity-purified antibody can be used to detect p85-sErbB3 using immunoblot, immunohistochemistry, immunoassay and other detection methods. One embodiment of the present invention pertains to immunoprecipitation followed by immunoblot analysis to detect p85-sErbB3 using anti-sErbB3 antibodies.

Another embodiment of the invention relates to a system and method of detecting p85-sErbB3 and other sErbB3 isoforms in a mammalian biological specimen selected from the group consisting of fluids, such as saliva, blood, serum, plasma, urine and ascites, solid tissues, and their derivatives.

Yet another embodiment of the invention relates to a vector for gene therapy, comprising a nucleic acid molecule having i) a transcription regulatory sequence; and ii) a second sequence coding for p85-sErbB3 or another sErbB3 isoform under transcriptional control of the transcription regulatory sequence; and iii) a delivery vehicle for delivering the nucleic acid molecule.

Those and other details, objects, and advantages of the present invention will become better understood or apparent from the following description and drawings showing embodiments thereof.

BRIEF DESCRIPTION OF THE FIGURES

The accompanying drawings illustrate examples of embodiments of the invention. In such drawings.

DESCRIPTION OF THE INVENTION

Figure 1:
FIG. 1. is a diagram of soluble ErbB3 (sErbB3) proteins. ErbB3 is composed of a 19 amino acid (aa) signal peptide sequence that is cleaved (gray box), an extracellular ligand-binding domain (aa 1-620), a transmembrane domain (aa 621-646; indicated as TM), and an intracellular domain (aa 647-1323). The extracellular domain of the receptor can be further divided into four subdomains (I-IV), as noted in the text. The alternate c-erbB3 transcripts arise from read-through of an intron and the use of alternative polyadenylation signals. p45-sErbB3 contains the amino-terminal 310 amino acids of ErbB3 and two unique carboxy-terminal amino acid residues. p50-sErbB3 contains the amino-terminal 351 amino acids of ErbB3 and 30 unique carboxy-terminal amino acid residues. p75-sErbB3 contains the amino-terminal 474 amino acids of ErbB3 and 41 unique carboxy-terminal amino acid residues. p85-sErbB3 contains the amino-terminal 519 amino acids of ErbB3 and 24 unique carboxy-terminal amino acid residues. The carboxy-terminal unique sequences are denoted as black boxes.

As used herein, the term "soluble" ErbB3 (sErbB3) means that the polypeptide is found in a form that is not anchored to the membrane of a cell via a typical transmembrane domain, i.e., a portion of the sErbB3 is not found physically embedded in the lipid bilayer which comprises the cell membrane.

As used herein, the term "biological activity" is defined to mean a polypeptide or a variant or fragment thereof, which has at least about 10%, preferably at least about 50%, and more preferably at least about 90% of the biological activity of the related polypeptide, such as for example the proteins having the amino acid sequence of SEQ ID NO:2 or SEQ ID NO: 4. The biological activity of a polypeptide of the invention can be measured by methods well known in the art including, but not limited to, the ability to bind heregulins or inhibit ErbB receptor mediated signaling.

As used herein, the term "protein" is a polypeptide, and the term "polypeptide" comprises at least two amino acids with no predefined limitation in length. sErbB3 polypeptides may be the complete sequence, for example SEQ ID NO:2 or SEQ ID NO:4, or may be corresponding fragments or variants thereof, such as the unique carboxy terminal region.

The terms "recombinant nucleic acid" or "preselected nucleic acid," "recombinant DNA sequence or segment" or "preselected DNA sequence or segment" refer to a nucleic acid that has been derived or isolated from any appropriate tissue source and that may be subsequently chemically altered, typically in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism and which is then chemically synthesized in essentially pure form. An example of such DNA "isolated" from a source would be a useful DNA sequence that is excised or removed from the source by chemical means, e.g., by the use of restriction endonucleases, so that it can be further manipulated, e.g., amplified for use in the invention by the methodology of genetic engineering.

"Regulatory sequences" is defined to mean RNA or DNA sequences necessary for the expression, post-transcriptional modification, translation, and post-translational modification of an operably linked coding sequence in a particular host organism. The control sequences that are suitable for prokaryotic cells, for example, include a promoter, and optionally an operator sequence, and a ribosome binding site. Eukaryotic cells are known to utilize promoters, stop sequences, enhancers, splicing, and polyadenylation signal sequences, as well as glycosylation and secretory signal sequences.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including avian, plant, insect, yeast, fungal or bacterial sources. Generally, the pre-selected DNA sequence is related to a DNA sequence that is resident in the genome of the host cell but is not expressed, or not highly expressed, or, alternatively, over-expressed.

The terms "transfected" or "transformed" are used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered DNA," "non-native DNA," or "foreign DNA," wherein the DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence which comprises a DNA encoding an sErbB3 isoform, for which the host cell may or may not express significant levels of autologous or "native" sErbB3.

A recombinant, functionally dominant-negative ErbB3 mutant with a deleted cytoplasmic domain, but which retains its transmembrane domain, can inhibit full-length ErbB2 and ErbB3 receptor activation (Ram, T. G., et al., 2000). In avian tissues, expression of a naturally occurring sEGFR/sErbB1 isoform inhibits TGFα dependent transformation. An aberrant soluble EGFR secreted by the A431 human carcinoma cell line also has been shown to inhibit the kinase activity of full-length EGFR. These soluble EGFR/ErbB1 receptors do not function as antagonists through high affinity ligand-binding. Herstatin, a naturally occurring soluble ErbB2 isoform inhibits ErbB2 receptor activation by blocking ErbB2 dimerization. In contrast, sErbB3, for example p85-sErbB3 and p45-sErbB3, inhibits HRG-induced stimulation of ErbB2, ErbB3, and ErbB4, at least in part, by neutralizing ligand activity through competitive binding.

The physiological role of p85-sErbB3 in normal tissues also has not been understood to date. As discussed in greater detail below, although a much higher concentration (100-fold) was required to inhibit cell growth, a 10-fold molar excess of p85-sErbB3 was sufficient to inhibit ErbB receptor phosphorylation. At this ratio of sErbB3 to full-length ErbB receptor, cell growth is stimulated by a small fraction of activated ErbB receptors that are still activated and sufficient for growth stimulation. It is known that the 2.1 kb transcript encoding p85-sErbB3 is expressed at low levels compared to the full-length c-erbB3 transcript in all cell lines and tissues examined to date. Research shows that local concentrations of autocrine growth factors such as EGF are exquisitely regulated and do not travel far from the cell surface from which they are released to exert their biological effects. In this context, tightly regulated localized concentrations of p85-sErbB3 have important consequences on cellular activities, such as HRG-mediated cell growth. These effects on cell growth are even more dramatic in cancer cells where cell polarity is typically lost, resulting in deregulation of normal spatial and temporal control of growth factor—growth factor receptor interactions because normal spatial cellular barriers are disrupted.

The present invention provides several novel isolated and purified nucleic acid sequences which encode isoforms of sErbB3 and nucleic acid sequences encoding engineered variants of these proteins. For example, disclosed herein are nucleic acids which specifically encode isoforms of sErbB3 whose amino acid sequences comprise the sequences of SEQ ID NO: 2 and SEQ ID NO: 4. Embodiments of the present invention relate to the use of sErbB3 as a unique HRG inhibitor because it can block HRG binding to cell surface ErbB receptors via binding to HRG with high affinity, thereby inhibiting HRG-induced stimulation of ErbB2, ErbB3, and ErbB4. This inhibition is sufficient to effectively block HRG-stimulated cell growth. These novel sErbB3 isoforms, therefore, are potent modulators of HRG regulated cell functions, such as proliferation, migration, and differentiation in normal mammalian and human tissues. Embodiments of the present invention also relate to regulation, either upregulation or downregulation, of heregulin activity using an sErbB3 agent.

Various embodiments of the invention relate to an sErbB3 agent for expression of sErbB3 or regulation, either upregulation or downregulation, of sErbB3 activity or expression (either transcription or translation). Examples of an sErbB3 agent include without limitation a polypeptide, a nucleic acid sequence (RNA or DNA, sense or antisense), an sErbB3 antibody, an expression vector, a small molecule, or a polypeptide agonist or antagonist.

Soluble ErbB3 also binds to ErbB receptors and regulates ErbB receptor signaling activities through downstream effectors such as MAPK, Akt, and PI3K. Additional embodiments of the present invention relate to regulation, either upregulation or downregulation, of ErbB receptor activities using an sErbB3 agent.

As further described below in the examples, sErbB3 is expressed in most epithelial tissues of many organs, including esophagus, liver, colon, stomach, thyroid, head and neck, kidney, bladder, pancreas, lung, skin, breast, ovary, uterus (cervix and endometruim), prostate gland, brain, intestine, or testis. Various embodiments of the present invention also relate to methods for treating cancer, such as carcinomas and gliomas, and cancer therapeutics comprising sErbB3 agents which regulate sErbB3 expression and/or function.

Nucleic Acid and Amino Acid Sequences.

The polypeptides in embodiments of the present invention may be in substantially pure form, isolated as a recombinant form, and may be fused to other moieties. Additional N-terminal or C-terminal sequences may be added to the polypeptides for various reasons, for example to improve expression or regulation of expression in particular expression systems, to provide protection against proteolytic cleavage, or to aid in identification as fusion proteins or purification such as affinity chromatography using fusion proteins. Techniques for providing such additional sequences are well known in the art. Furthermore polypeptides with additional N-terminal or C-terminal sequences may simply result from the technique used to obtain the polypeptide without providing any advantageous characteristics and are also within the scope of the present invention. Whatever sequence is added, the resultant polypeptide preferably exhibits the biological activity of the cognate sErbB3, for example a polypeptide having the amino acid sequence SEQ ID NO: 2 or SEQ ID NO: 4.

The polypeptides of the present invention include post-translational modifications, for example and without limitation, phosphorylation, glycosylation and farnesylation.

Furthermore, alterations, either conservative or non-conservative, can occur in the amino acid sequence of a polypeptide, which likely do not affect the function. Such alterations include amino acid deletions, insertions, and substitutions. Such alterations can result from alternative splicing and/or the presence of multiple translation start sites and/or stop sites. Polymorphisms may also arise as a result of the infidelity which is inherent in the translation process. Conservative substitutions are preferred. As such, the amino acids glycine, alanine, valine, leucine and isoleucine are often substituted for one another. Of these possible substitutions, it is preferred that glycine and alanine are used to substitute for one another because they have relatively short aliphatic side chains and that valine, leucine and isoleucine are used to substitute for one another because they have larger hydrophobic aliphatic side chains. Other amino acids that are often substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur-containing side chains). Aspartic acid and glutamic acid can substitute for phosphoserine and phosphothreonine, respectively (amino acids with acidic side chains). Amino acid substitutions or insertions can be made using naturally occurring or non-naturally occurring amino acids; however, L-amino acids are preferred in one embodiment.

Whatever amino acid changes are made, whether by means of substitution, modification, insertion or deletion, polypeptides embodied within embodiments of the present invention have at least 50% sequence identity with the related sErbB3 isoform, for example isoforms comprising SEQ ID NO: 2 or SEQ ID NO: 4, and in various embodiments the degree of sequence identity is at least 75%. In various embodiments, sequence identities of at least 80%, 85%, 90%, 95%, 98% or 99% are used.

Amino acid sequence variants of an sErbB3 or fragments thereof can be prepared by a number of techniques, such as random mutagenesis of DNA which encodes an sErbB3 or a region thereof. Useful methods also include PCR mutagenesis, cassette mutagenesis, and saturation mutagenesis. A library of random amino acid sequence variants can also be generated by the synthesis of a set of degenerate oligonucleotide sequences. Non-random or directed mutagenesis techniques can be used to provide specific sequences or mutations in specific regions. Alanine scanning mutagenesis is a useful method for identification of certain residues or regions of the desired protein that are preferred locations or domains for mutagenesis, see for example Cunningham and Wells (Science 244:1081-1085, 1989). Oligonucleotide-mediated mutagenesis is a useful method for preparing substitution, deletion, and insertion variants of DNA, see, e.g., Adelman et al., (DNA 2:183, 1983). Additionally, in another example, combinatorial mutagenesis is used to generate variants.

Embodiments of the present invention further relate to variants of the nucleic acid sequences, for example nucleic acid sequences SEQ ID NO:1 and SEQ ID NO: 3, which encode proteins, analogs or derivatives of an sErbB3, for example p85-sErbB3 and p45-sErbB3. Such nucleic acid variants are produced by nucleotide substitutions, deletions, or additions and may involve one or more nucleotides.

In examples, the nucleic acid sequence is a genomic sequence or a cDNA sequence. The nucleotide sequence includes, for example: an sErbB3 coding region; a promoter sequence, such as a promoter sequence from an sErbB3 gene or from another gene; an enhancer sequence; untranslated regulatory sequences either 5' or 3' from an sErbB3 gene or from another gene; a polyadenylation site; and an insulator sequence. The nucleotides of embodiments of the present invention can be modified at the base moiety, sugar moiety or phosphate backbone to improve the stability, hybridization, or solubility of the molecules. For instance, the deoxyribose phosphate backbone of the polynucleotide molecules is modified to generate peptide polynucleotides (see, for example Hyrup et al, Bioorganic & Medicinal Chemistry, 4:523, 1996). As used herein, the terms "peptide polynucleotides" or "PNAs" refer to polynucleotide mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. In examples, PNA oligomers are synthesized using standard solid phase peptide synthesis protocols. PNAs are used in therapeutic and diagnostic applications. For example, PNAs are used as antisense agents for sequence-specific modulation of gene expression.

In other examples, the unique sErbB3 sequences are also used as a target for selective inhibition of expression (stability, transcription, or translation) using siRNA, RNAi, short hairpin RNA, microRNAs, ribozyme, and triple helix methodologies, as well as antisense sequences, including antisense oligonucleotides. Useful fragments of the sErbB3 nucleic acid sequences include antisense or sense oligonucleotides comprising a single-stranded nucleic acid sequence (either RNA or DNA) capable of binding to target sErbB3 mRNA or sErbB3 DNA sequences. Antisense or sense oligonucleotides comprise a fragment of the coding region of an sErbB3, for example to a unique region such as the C-terminus. Such a fragment generally comprises at least about 5 nucleotides, and typically 14 to 30 nucleotides. The ability to derive an antisense or a sense oligonucleotide, based upon a cDNA sequence encoding a given protein is well known in the art and is described in, for example, Stein and Cohen (Cancer Res. 48:2659, 1988), van der Krol et al. (Bio Techniques 6:958, 1988), Izant J. G. and Weintraub H., (Cell, 36: 100.7-1015, 1984) and Rosenberg et al. (Nature, 313:703-706, 1985).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Thus, the antisense oligonucleotides are used for example to block expression of sErbB3 proteins. Antisense or sense oligonucleotides further comprise oligonucleotides having modified sugar-phosphodiester backbones or other sugar linkages, and wherein such sugar linkages are resistant to endogenous nucleases. Such oligonucleotides with resistant sugar linkages are stable in vivo, i.e., capable of resisting enzymatic degradation, but retain sequence specificity to be able to bind to target nucleotide sequences.

Other examples of sense or antisense oligonucleotides include oligonucleotides which are covalently linked to other organic moieties, such as for example organic moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

In other examples, sense or antisense oligonucleotides are introduced into a cell containing the target nucleotide sequence by formation of a conjugate with a ligand binding molecule, for example cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

These sense and antisense nucleic acid sequences have utility as therapeutic agents, in methods of treating cancer or other diseases and medical conditions, and in methods of regulating sErbB3 expression.

The sequences embodied herein relate specifically to sErbB3 isoforms, for example SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. Various embodiments relate to the unique C-terminal region of the sErbB3 isoforms, for example variants and fragments specific to the unique region.

Expression Vectors and Methods of Delivery

Other embodiments of the present invention comprise an expression vector containing a nucleic acid sequence that expresses an sErbB3 polypeptide, for example a polypeptide having an amino acid sequence comprising SEQ ID NO:2 or SEQ ID NO:4, in a suitable host. In an example, the nucleic acid sequence has a promoter operably linked to the polypeptide coding region, the promoter being inducible or constitutive and, optionally, cell-type or tissue-specific. In an example, the promoter may also be a heterologous promoter. The vector may be, for example, a plasmid, a single or double-stranded phage vector, or a single or double-stranded viral RNA or DNA molecule. An example of an inducible vector is a vector induced for expression by environmental factors that are easy to manipulate, such as temperature and nutrient additives. Examples of viral vectors include viruses such as baculoviruses, papova viruses such as SV40, vaccinia viruses, adenoviruses including adeno-associated viruses, fowl pox viruses, lentiviruses, parvoviruses, herpes simplex viruses, pseudorabies viruses, and retroviruses, as well as vectors derived from combinations thereof, such as those derived from plasmid and bacteriophage genetic elements, such as cosmids and phagemids.

Embodiments of the present invention also include therapeutic expression of genetic material, including gene therapy expression of an sErbB3 isoform, variant, or fragment. Gene therapy is either by in vivo gene therapy, which is direct delivery of the nucleic acid or nucleic acid-carrying vector into a patient, or ex vivo gene therapy, which is indirect delivery to the patient via transplanted cells that were first transformed with the nucleic acid sequences or nucleic acid-carrying vector in vitro. In examples, viral vectors such as the examples listed herein can be used for in vivo and ex vivo gene therapy.

Plasmid DNA can be delivered with the help of, for example and without limitation: cationic liposomes such as lipofectin, or derivatized (e.g. antibody conjugated) polylysine conjugates, nanoparticles, gramacidin S, artificial viral envelopes or other such intracellular carriers, as well as direct injection of the gene construct or $CaPO_4$ precipitation carried out in vitro.

In other examples, a subject polynucleotide is administered using a non-viral delivery vehicle. "Non-viral delivery vehicle" (also referred to herein as "non-viral vector") as used herein is meant to include chemical formulations containing naked or condensed polynucleotides (e.g., a formulation of polynucleotides and cationic compounds, for example dextran sulfate), and naked or condensed polynucleotides mixed with an adjuvant such as a viral particle (i.e., the polynucleotide of interest is not contained within the viral particle, but the transforming formulation is composed of both naked polynucleotides and viral particles, see, for example Curiel et al. 1992 µm. J. Respir. Cell Mol. Biol. 6:247-52. Thus "non-viral delivery vehicle" includes vectors composed of polynucleotides plus viral particles where the viral particles do not contain the polynucleotide of interest. "Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed for example by Felgner et al (U.S. Pat. Nos. 5,264,618 and 5,459,127; PNAS 84:7413-7417, 1987; Annals N.Y. Acad. Sci. 772:126-139, 1995), DDAB, DOPC, and phospholipids such as phophatidylcholine. In other examples, lipid based vehicles consist of neutral or negatively charged phospholipids or mixtures thereof including artificial viral envelopes as disclosed for example by Schreier et al. (U.S. Pat. Nos. 5,252,348 and 5,766,625).

Non-viral delivery vehicles include polymer-based carriers, including natural and synthetic polymers and co-polymers. Preferably, the polymers are biodegradable or are readily eliminated from the subject. Naturally occurring polymers include polypeptides and polysaccharides. Synthetic polymers include, but are not limited to, polylysines and polyethyleneimines (PEI; see for example Boussif et al., PNAS 92:7297-7301, 1995) which molecules can also serve as condensing agents. These carriers are dissolved, dispersed or suspended in a dispersion liquid such as water, ethanol, saline solutions and mixtures thereof. A wide variety of synthetic polymers are known in the art.

In examples, naked DNA or RNA molecules are used where they are in a form which is resistant to degradation, such as by modification of the ends, by the formation of circular molecules, or by the use of alternate bonds including phosphothionate and thiophosphoryl modified bonds. In other examples, the delivery of nucleic acids is facilitated by transport where the nucleic acid molecules are conjugated to polylysine or transferrin.

Antisense or sense oligonucleotides are introduced into a cell containing the target nucleic acid sequence by any genetic material transfer method, including, for example, $CaPO_4$-mediated DNA transfection, lipid mediated transfection, electroporation, or by using gene transfer vectors or methods described above. In another example, an antisense or sense oligonucleotide is inserted into a suitable viral vector, such as those described previously. A cell containing the target nucleic acid sequence is contacted with the recombinant viral vector, either in vivo or ex vivo.

Detection/Diagnosis

Other embodiments of the present invention relate to methods for detecting an sErbB3 and assessing the risk of developing a preneoplastic lesion or cancer, screening for a cancer, or diagnosing a cancer. Additional embodiments of the present invention relate to assaying a biological sample for an sErbB3 to evaluate prognosis, theragnosis, responsiveness to a treatment of cancer, prophylactic selection of a cancer prevention regimen, early detection of a cancer, or cancer progression, recurrence, or metastasis. One embodiment relates to a method of assaying for an sErbB3 and/or diagnosing a cancer in a subject, for example a human or other mammal, which comprises the step of detecting and/or quantifying a concentration of a polypeptide or nucleic acid sequence of the invention in a biological sample obtained from said subject. Examples of biological samples include fluids, such as saliva, blood, serum, plasma, urine and ascites, solid tissues, and their derivatives. In an example, antibodies which recognize a polypeptide of the invention are used to detect the amount of the polypeptide in a biological sample such as serum.

In one embodiment, binding of an sErbB3 antibody in tissue sections can be used to detect aberrant polypeptide localization or an aberrant concentration of polypeptide. In another embodiment, an antibody to a polypeptide of the invention can be used to assay a subject sample, for example tissue or serum, for the concentration of the polypeptide where an aberrant amount of polypeptide is indicative of a risk of developing a preneoplastic lesion or cancer, prognosis, theragnosis, responsiveness to treatment, prophylactic selection of a cancer prevention regimen, early detection of a cancer, or cancer progression, recurrence, or metastasis. As used herein, an "aberrant amount" means an amount that is increased or decreased compared with the amount in a subject free from cancer or an established reference level.

Examples of suitable immunoassays for detecting or assaying sErbB3 include, without limitation, competitive and non-competitive assay systems using techniques such as western blots, radioimmunoassays, ELISA (enzyme linked immunosorbent assay), acridinium-linked immunosorbent assays (ALISA), "sandwich" immunoassays, immunohistochemical assays, immunofluorescent detection assays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Immunoassays to detect and quantitate an sErbB3, for example p85-sErbB3, have been developed for use on formalin-fixed, paraffin-embedded tissue and tumor samples and for use on frozen-section tissue and tumor samples. In addition, antibodies can be used to selectively quantitate an sErbB3 polypeptide in other tissues, including for example saliva, blood, serum, plasma, and urine, using enzyme-linked immunosorbent assays, acridinium-linked immunosorbent assays, and radioimmunoassay. Such assays may be combined with the quantitative assessment of other biomarkers on a similar platform (e.g., multiplex assays) to increase the biological or clinical information obtained.

Quantitation of the expression of the specific mRNA encoding the polypeptide can be performed using methods such as RNA in situ hybridization (RNA ISH), as well as other complementary RNA methodologies, such as RNAse protection assays. Genetic aberrations in the relative copy number of the sequence can be performed by any genomic DNA detection method, for example FISH.

Antibodies

Soluble ErbB3 polypeptides embodied within the present invention can be "antigenic" and/or "immunogenic". Generally, "antigenic" means that the polypeptide is capable of being used to generate antibodies or indeed is capable of inducing an antibody response in a subject. "Immunogenic" means that the polypeptide is capable of eliciting an immune response in a subject. For example, the polypeptide could not only generate an antibody or anti-idiotypic antibody response but, in addition, non-antibody based immune responses, and also could be used to produce a therapeutic vaccine. In an example, the unique C-terminal region of an sErbB3 is a target of the vaccine.

Further embodiments relate to antibodies, which specifically bind an sErbB3 isoform, generated using an immunogen derived from the sErbB3 isoform, such as from an isoform having SEQ ID NO: 2, SEQ ID NO: 4, SEQ ID NO: 6, or SEQ ID NO: 8. In an example, an antibody specific to the sErbB3 is generated using the unique C-terminal region (described herein) of the specific sErbB3, such as amino acids 540-562 of SEQ ID NO: 2, a 23 aa sequence (Ser Lys Gly Ser Gln Ser Arg Met Gly Gly Gly Gly Ala Leu Gln Trp Asn Cys Ser Gly Gly Ile Gln) from the unique C-terminal sequence of p85-sErbB3. Such antibodies include, but are not limited to polyclonal, monoclonal, bispecific, humanized or chimeric antibodies, single chain antibodies, Fab fragments and F(ab') fragments, fragments produced by a Fab expression library, anti-idiotypic (anti-Id) antibodies, affibodies, and epitope-binding fragments of any of the above. As used herein, "antibody" refers to immunoglobulin molecules and immunologically active portions of immunoglobulin molecules, i.e., molecules that contain an antigen binding site that specifically binds an antigen. The immunoglobulin molecules can be of any class, e.g., IgG, IgE, IgM, IgD and IgA, or subclass of immunoglobulin molecule. As described above, such antibodies are used for detection and quantification as well as in methods of treating cancer, methods of regulating sErbB3 isoforms, and cancer therapeutics.

In the production of antibodies, screening for the desired antibody is accomplished by techniques known in the art, e.g., ELISA (enzyme-linked immunosorbent assay). In one example, to select antibodies which recognize a specific domain of a polypeptide of the invention, generated hybridomas are assayed for reactivity toward a product which binds to a polypeptide fragment of the sErbB3 isoform.

Polyclonal antibodies directed towards a sErb3 polypeptide are generated by stimulating their production in a suitable animal host (e.g. a chicken, mouse, rat, guinea pig, rabbit, sheep, goat or monkey) when a polypeptide of embodiments of the present invention is injected into the animal. If necessary, an adjuvant may be administered together with the polypeptide of the invention. The antibodies are then purified by virtue of high affinity binding to the associated polypeptide of the invention.

Monoclonal antibodies (mAbs) directed toward an sErbB3 polypeptide may be generated by any technique known to those skilled in the art to provide for the production of antibody molecules by continuous cell lines in culture. Some examples for producing mAbs include the hybridoma technique (Kohler and Milstein, 1975, Nature 256:495-497), the trioma technique, the human B-cell hybridoma technique (Kozbor et al., 1983, Immunology Today 4:72), the EBV-hybridoma technique to produce human monoclonal antibodies (Cole et al., 1985, Monoclonal Antibodies and Cancer Therapy, Alan R. Liss, Inc., pp. 77-96), and germ-free animals (PCT/US90/02545). The hybridoma producing the mAbs of the invention may be cultivated in vitro or in vivo. The mAbs to sErbB3 include but are not limited to human mAbs and chimeric mAbs (e.g., human-mouse chimeras). A chimeric antibody is a molecule in which different portions are derived from different animal species, such as those having a human immunoglobulin constant region and a variable region derived from a murine mAb. See, for example, U.S. Pat. No. 4,816,567; and U.S. Pat. No. 4,816,397. Humanized antibodies are antibody molecules from non-human species having one or more complementarity determining regions (CDRs) from the non-human species and a framework region from a human immunoglobulin molecule. See, for example, U.S. Pat. No. 5,585,089.

Chimeric and humanized mAbs can be produced by recombinant DNA techniques known in the art, for example and without limitation using methods described in WO 87/02671; EP 184,187; EP 171,496; EP 173,494; WO 86/01533; U.S. Pat. No. 4,816,567; EP 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060; Neuberger et al., 1984, Nature 312:604-608; Takeda et al., 1985, Nature 314:452-454).

For therapeutics and methods of treating human patients, completely human sErbB3 antibodies are desirable. Such antibodies can be generated, for example, using transgenic mice which are incapable of expressing endogenous immunoglobulin heavy and light chain genes, but which can express human heavy and light chain genes. The transgenic mice are immunized by methods known to those skilled in the art with a selected antigen, e.g., all or a portion of an sErbB3 specific polypeptide, for example SEQ ID NO:2, SEQ ID NO: 4, SEQ ID NO: 6, SEQ ID NO: 8 or a unique C-terminal sequence, such as the unique 24 aa C-terminal sequence of p85-sErbB3 (for example, amino acids 539-562 of SEQ ID NO: 2: Tyr Ser Lys Gly Ser Gln Ser Arg Met Gly Gly Gly Gly Ala Leu Gln Trp Asn Cys Ser Gly Gly Ile Gln). Then, mAbs directed against the antigen can be obtained using conventional hybridoma technology where the human immunoglobulin transgenes harbored by the transgenic mice rearrange during B cell differentiation, and subsequently undergo class switching and somatic selection. By using such a technique, therapeutically useful IgG, IgA, IgM, IgD and IgE antibodies can be produced. For references and protocols for producing human antibodies, see, for examples Lonberg and Huszar (1995, Int. Rev. Immunol. 13:65-93); U.S. Pat. No. 5,625, 126; U.S. Pat. No. 5,633,425; U.S. Pat. No. 5,569,825; U.S. Pat. No. 5,661,016; and U.S. Pat. No. 5,545,806.

Furthermore, completely human antibodies which recognize a selected epitope can be produced, for example, by the "guided selection" technique in which a selected non-human mAb, e.g., a mouse antibody, is used to guide the selection of a completely human antibody recognizing the same epitope such as disclosed in Jespers et al. (1994) Biotechnology 12:899-903.

The sErbB3 antibodies embodied herein also can be generated using various phage display methods known in the art whereby functional antibody domains are displayed on the surface of phage particles which carry the polynucleotide sequences encoding the functional antibody domains. After phage selection, which is performed for example by using labeled antigen or antigen bound or captured to a solid surface or bead, the antibody coding regions from the phage can be isolated and used to generate whole antibodies, including human antibodies, or any other desired antigen binding fragment, and expressed in any desired host, including mammalian cells, insect cells, plant cells, yeast, and bacteria. Techniques known in the art to recombinantly produce Fab, Fab' and F(ab')2 fragments can also be employed.

Single-chain Fvs and antibodies which bind an sErbB3 also can be produced by methods known in the art, such as for example those disclosed in U.S. Pat. No. 4,946,778 and U.S. Pat. No. 5,258,498; Huston et al., Methods in Enzymology 203:46-88 (1991); Shu et al., PNAS 90:7995-7999 (1993); and Skerra et al., Science 240:1038-1040 (1988).

Further, bispecific antibodies which bind to an sErbB3 can be made by methods known in the art and are embodied herein. For example, bispecific antibodies comprise a hybrid immuoglobulin heavy chain with a first binding specificity in one arm, and a hybrid immunoglobulin heavy chain-light chain pair with a second binding specificity in the other arm. See, for example WO 94/04690 and Suresh et al., Methods in Enzymology, 1986, 121:210.

Embodiments of the present invention include functionally active fragments, derivatives or analogs of the anti-polypeptide immunoglobulin molecules. "Functionally active" means that the fragment, derivative or analogue is able to elicit anti-anti-idiotype antibodies (i.e., tertiary antibodies) that recognize the same antigen that is recognized by the antibody from which the fragment, derivative or analogue is derived. In an example, the antigenicity of the idiotype of the immunoglobulin molecule is enhanced by deletion of framework and CDR sequences that are C-terminal to the CDR sequence that specifically recognizes the antigen. To determine which CDR sequences bind the antigen, synthetic peptides containing the CDR sequences are used in binding assays with the antigen by any binding assay method known in the art.

Embodiments of the present invention include antibody fragments such as, but not limited to, F(ab')2 fragments and Fab fragments. In examples, antibody fragments which recognize specific epitopes are generated by known techniques to those skilled in the art. F(ab')2 fragments consist of the variable region, the light chain constant region and the CH1 domain of the heavy chain and are generated by pepsin digestion of the antibody molecule. Fab fragments are generated by reducing the disulphide bridges of the F(ab').sub.2 fragments. Further, any other molecule with the same specificity as the antibodies and antibody fragments of embodiments of the present invention are embodied herein.

Embodiments of the present invention also relate to heavy chain and light chain dimers of the antibodies of the invention, or any minimal fragment thereof such as Fvs or single chain antibodies (SCAs). See for example U.S. Pat. No. 4,946,778; Bird, 1988, Science 242:42342; Huston et al., 1988, Proc. Natl. Acad. Sci. USA 85:5879-5883; and Ward et al., 1989, Nature 334:544-54. Single chain antibodies are formed by linking the heavy and light chain fragments of the Fv region via an amino acid bridge, resulting in a single chain polypeptide. Techniques for the assembly of functional Fv fragments in E. coli may be used such as the method disclosed in Skerra et al., (1988, Science 242:1038-1041).

Additional embodiments of the present invention provide for fusion polypeptides of the immunoglobulins of embodiments of the invention, or functionally active fragments thereof, for example in which the immunoglobulin is fused via a covalent bond (e.g., a peptide bond), at either the N-terminus or the C-terminus to an amino acid sequence of another polypeptide (or portion thereof, which is at least 10, 20 or 50 amino acids in length) that is not the immunoglobulin. The immunoglobulin, or fragment thereof, may be covalently linked to the other polypeptide at the N-terminus of the constant domain. Such fusion polypeptides may facilitate purification, increase half-life in vivo, and enhance the delivery of an antigen across an epithelial barrier to the immune system.

The immunoglobulins of embodiments of the invention include analogues and derivatives that are modified, such as by the covalent attachment of any type of molecule as long as such covalent attachment does not impair specific binding. For example without limitation, the derivatives and analogues of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein. In examples, chemical modifications of the analogues and derivatives are carried out by known techniques including, but not limited to, specific chemical cleavage, acetylation, and formylation. In additional examples, the analogues or derivatives contain one or more non-classical amino acids.

In various embodiments, the sErbB3 antibodies described herein are used in methods known in the art relating to the localization and activity of the polypeptides of embodiments of the invention. Examples of use include without limitation, imaging or radioimaging these polypeptides, measuring amounts thereof in appropriate biological samples, in diagnostic, prognostic, and theragnostic methods, and for radiotherapy.

The antibodies of embodiments of the invention can be produced by any method known in the art for the synthesis of antibodies, in particular, by chemical synthesis or by recombinant expression, and may be produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid sequence encoding the antibody may be assembled from chemically synthesized oligonucleotides, as described for example in Kutmeier et al. (1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody is obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

Once a nucleic acid encoding at least the variable domain of the antibody molecule is obtained, it may be introduced into a vector containing the nucleotide sequence encoding the constant region of the antibody molecule. Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute or delete the one or more variable region cysteine residues participating in an intrachain disulphide bond with an amino acid residue that does not contain a sulfhydryl group. Such modifications can be carried out by any method known in the art for the introduction of specific mutations or deletions in a nucleotide sequence, for example, but not limited to, chemical mutagenesis, in vitro site directed mutagenesis, or PCR based methods.

Once a nucleic acid encoding an antibody of the invention has been obtained, the vector for the production of the antibody may be produced by recombinant DNA technology using techniques well known in the art. Such methods can be used to construct expression vectors containing an antibody molecule coding sequence and appropriate transcriptional and translational control signals. These methods include, for example without limitation, in vitro recombinant DNA techniques, synthetic techniques, and in vivo genetic recombination. See, for example, the techniques disclosed in Sambrook et al. (2001, Molecular Cloning, A Laboratory Manual, 3d Ed., Cold Spring Harbor Laboratory, Cold Spring Harbor, N.Y.) and Ausubel et al. (Current Protocols in Molecular Biology, John Wiley & Sons, NY).

A variety of host-expression vector systems can be utilized to express an antibody molecule of embodiments of the invention. Such host-expression systems represent vehicles by which the coding sequences of interest may be produced in large quantity and subsequently purified, but also represent cells which may, when transformed or transfected with the appropriate nucleotide coding sequences, express the antibody molecule of the invention in situ. These include but are not limited to microorganisms such as bacteria (e.g., *E. coli* or *B. subtilis*) transformed with recombinant bacteriophage DNA, plasmid DNA or cosmid DNA expression vectors containing antibody coding sequences; yeast (e.g., *Saccharomyces* or *Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, HEK 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a polypeptide is to be produced for the generation of pharmaceutical compositions comprising an antibody molecule, vectors which direct the expression of high levels of fusion polypeptide products that are readily purified may be desirable. Such vectors include but are not limited to the *E. coli* expression vector pUR278 (Ruther et al., 1983, EMBO J. 2:1791) in which the antibody coding sequence may be ligated individually into the vector in frame with the lac Z coding region so that a fusion polypeptide is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion polypeptides with glitathione S-transferase (GST). In general, such fusion polypeptides are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system or those-described above) may be utilized.

As discussed above, a host cell strain may be chosen which modulates the expression of the inserted sequences, or modifies and processes the gene product in a specific way. Such modifications (e.g., glycosylation) and processing (e.g., cleavage) of polypeptide products may be important for the function of the polypeptide.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable marker (e.g., neomycin or hygromycin), and selecting for expression of the selectable marker. Such engineered cell lines may be particularly useful for screening and evaluation of agents that interact directly or indirectly with the antibody molecule.

The expression levels of the antibody molecule can be increased by vector amplification.

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is preferably placed before the heavy chain to avoid an excess of toxic free heavy chain (see, e.g. Proudfoot, 1986, Nature 322:52; Kohler, 1980, Proc. Natl. Acad. Sci. USA 77:2197). The coding sequences for the heavy and light chains comprise either cDNA or genomic DNA.

Once the antibody molecule has been recombinantly expressed, it may be purified by any method known in the art for purification of an antibody molecule, for example without limitation, by chromatography (e.g., ion exchange chromatography, affinity chromatography such as with protein A or specific antigen, and sizing column chromatography), centrifugation, differential solubility, or by any other standard technique for the purification of polypeptides.

In another embodiment, antibodies of the invention or fragments thereof are conjugated to a diagnostic or therapeutic moiety. The antibodies are used for diagnosis or to determine the efficacy of a given treatment regimen. Detection is facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

The therapeutic moiety is not to be construed as limited to classical chemical therapeutic agents. In an example, the moiety may be a protein or polypeptide possessing a desired biological activity. Such proteins may include, for example, a toxin such as abrin, ricin A, pseudomonas exotoxin, or diphtheria toxin; a polypeptide such as tumour necrosis factor, $\alpha$-interferon, $\beta$-interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moieties to antibodies are well known to those skilled in the art, see for example without limitation, e.g., Arnon et al., "Monoclonal Antibodies For immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, in another example, an antibody is conjugated to a second antibody to form an antibody heteroconjugate as disclosed for example in U.S. Pat. No. 4,676,980.

An antibody with or without a therapeutic moiety conjugated to it can be used as a therapeutic that is administered alone or in combination with cytotoxic factor(s) and/or cytokine(s).

Screening

Embodiments of the invention include methods for identifying active agents (e.g., chemical compounds, proteins, or peptides) that bind to an sErbB3 polypeptide of embodiments of the invention and/or have a stimulatoly or inhibitory effect on the expression or activity of an sErbB3 polypeptide of the invention. Examples of active agents, include, but are not limited to, nucleic acids (e.g., DNA and RNA), carbohydrates, lipids, proteins, peptides, peptidomimetics, agonists, antagonists, small molecules and other drugs. Active agents can be obtained using any of the numerous suitable approaches in combinatorial library methods known in the art, including without limitation: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, for examples, methods disclosed in Lam, 1997, Anticancer Drug Des. 12:145; U.S. Pat. No. 5,738,996; and U.S. Pat. No. 5,807,683.

Various techniques are known in the art for screening polypeptides that interact with a protein such as sErbB3. Examples of polypeptides include synthetic peptides, small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecule, binding to natural ligands, e.g., a receptor or substrate, facilitates relatively easy isolation of the vector encoding the gene whose product was detected. Examples include without limitation: two hybrid (interaction trap) assays, display libraries in which the candidate peptides are displayed on the surface of a cell, plasmid, or viral particle, and the ability of particular cells or viral particles to bind an appropriate receptor protein via the displayed product is detected in a "panning assay". In an example, such high through-put assays are followed or substituted by secondary screens, such as binding assays, to determine biological activities and differentiate agonists from antagonists.

Therapeutics and Methods of Treating

Methods and therapeutics to regulate sErbB3 in cancers, such as carcinomas and gliomas, with aberrant sErbB3 expression or activity or which are regulated by HRG signaling or ErbB activity are embodied herein. Such cancers include without limitation esophageal, liver, colon, gastric, thyroid, head and neck, kidney, bladder, pancreatic, lung, skin, breast, ovarian, cervical, endometrial, prostate, brain, intestinal, or testicular.

Various embodiments of the present invention include methods and therapeutics to treat cancer, including carcinomas and gliomas, using an sErbB3 agent to regulate an sErbB3 by any available means including without limitation nucleic acids (e.g., DNA and RNA), carbohydrates, lipids, proteins, peptides, peptidomimetics, agonists, antagonists, small molecules and other drugs. For example, various embodiments of the present invention pertain to regulation of p85-sErbB3 and/or p45-sErbB3 or other sErbB3 isoforms. For example, the methods and therapeutics of the present invention comprise administering the nucleic acid sequences SEQ ID NO:1 or SEQ ID NO: 3, or a complementary sequence thereof, or the amino acid sequences SEQ ID NO: 2 or SEQ ID NO: 4. The sequences include for example, without limitation and as more fully described supra, the complete sequence, fragments and variants, as well as antisense oligonucleotides. Additional embodiments of the present invention include methods to regulate heregulin or ErbB signaling activity through regulation of an sErbB3 agent. Effective amounts of an sErbB3 or an agonist or antagonist of an sErbB3 (function or expression) can be determined, for example, by decreased or increased heregulin activity, respectively as well as by effects on other biological endpoints such as receptors, downstream mediators, or biochemical targets such as cell survival, cell growth, or metastasis.

One embodiment of the present invention relates to a method of treating cancer in a subject, such as a human. The method includes administering to the subject an agent that regulates an sErbB3 (function or expression), such as p85-sErbB3 or p45-sErbB3, in an amount sufficient to reduce or prevent carcinoma cell growth and/or metastasis. The sErbB3 agent may be administered in an amount effective to regulate heregulin activation of ErbB receptor signaling activity, as well as by effects on other biological endpoints such as receptors, downstream mediators, or biochemical targets such as cell survival, cell growth, or metastasis.

In examples, the agent comprises any of the previously described polypeptides, nucleic acid sequences, or variants thereof or previously described instruments. Examples include without limitation an sErbB3 polypeptide, or a functional fragment, variant or analog thereof having an sErbB3 activity; a polypeptide agonist or antagonist of sErbB3 that increases or decreases respectively the activity of an sErbB3 or the binding of an sErbB3 to a binding partner; a small molecule that increases or decreases expression of an sErbB3, for example by binding to the promoter region of the ErbB3 gene; an antibody, for example an antibody that binds to and stabilizes or assists the binding of sErbB3 to an sErbB3 binding partner or an antibody that inhibits binding to and destabilizes the binding of sErbB3 to an sErbB3 binding partner; or a nucleotide sequence encoding an sErbB3 polypeptide or functional fragment or analog thereof. The agent and instruments described herein also may comprise any compositions or methods in molecular medicine or therapeutic transfer of genetic material known to those skilled in the art such as those previously described above to achieve a therapeutic effect.

In an embodiment, the amount of sErbB3 protein is increased by elevated transcriptional expression of the endogenous sErbB3 gene and translation of the sErbB3 isoform from its alternate mRNA or by increasing sErbB3 mRNA stability. In another embodiment, transcription of the sErbB3 gene is increased for example by altering its regulatory sequence such as by the addition of a positive regulatory element (such as an enhancer or a DNA-binding site for a transcriptional activator); the deletion of a negative regulatory element (such as a DNA-binding site for a transcriptional repressor); and/or replacement of the endogenous regulatory sequence, or elements therein, with that of another gene, thereby allowing the coding region of the ErbB3 gene to be transcribed more efficiently. In other examples, the amount of sErbB3 protein is regulated post-transcriptionally by microRNAS or post-transcriptional regulatory elements.

In an embodiment, the agent is a vector that includes a nucleic acid sequence encoding an sErbB3, preferably a human sErbB3, for example SEQ ID NO: 2 or SEQ ID NO:4. The vector can be any vector suitable for transfer of genetic material such as those listed previously or that are known in the art.

In other embodiments, a therapeutic treatment or composition comprises essentially the agent.

The agent can be administered by any method known in the art, for example by direct administration, e.g., injection, intravenous or intramuscular. In another example, the agent is delivered directly to an affected tissue. The agent can be coupled to a second agent, for example a delivery agent (e.g., an agent that protects the agent from degradation) or a targeting agent (e.g., for targeting to the cancer or affected tissue or targeting to the inside of a cell). Targeting may occur by means of, for example, the gene delivery vehicle, cell-type or tissue-type expression due to the transcriptional regulatory sequences controlling expression of the receptor gene, or a combination thereof.

The agent, e.g., an sErbB3 nucleic acid molecule, polypeptide, fragments or analog, or modulators (e.g., organic compounds and antibodies) can be incorporated into pharmaceutical compositions suitable for administration to a subject, for example a human. Such compositions may include the agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The compositions may additionally include solubilizing agents, lubricating agents, wetting agents, sweeteners, colorants, odorants, salts (polypeptides of embodiments of the present invention may themselves be provided in the form of a pharmaceutically acceptable salt), buffers, coating agents, antioxidants, flavoring agents, emulsifiers, preservatives and the like.

A pharmaceutical carrier for hydrophobic compounds of embodiments of the invention is a co-solvent system comprising benzyl alcohol, a nonpolar surfactant, a water-miscible organic polymer, and an aqueous phase. The proportions of a co-solvent system may be varied considerably without destroying its solubility and toxicity characteristics.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Solutions or suspensions used for parenteral application can include the following components: a sterile diluent such as water for injection, saline solution, fixed oils, polyethylene glycols, glycerine, propylene glycol or other synthetic solvents, suspending agents, or thickening agents; antibacterial agents such as benzyl alcohol or methyl parabens; antifungal agents such as parabens or thimerosal; antioxidents such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral composition can be enclosed in ampoules, disposable syringes or multiple dose vials made of glass or plastic. The composition may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Prolonged adsorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation may include vacuum drying and freeze-drying which yields a powder of the active ingredient plus any additional desired ingredient from a previously sterile-filtered solution thereof.

Pharmaceutical compositions comprised of an sErbB3 agent adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include, for example, vegetable oils, waxes, fats, semi-solid, or liquid polyols etc. For the preparation of solutions and syrups, excipients which may be used include, for example, water, polyols and sugars. For the preparation of suspensions, oils (e.g. vegetable oils) may be used to provide oil-in-water or water-in-oil suspensions.

Pharmaceutical compositions comprised of the sErbB3 agent adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6):318 (1986).

Pharmaceutical compositions comprised of an sErbB3 agent adapted for topical administration may be formulated as ointments, creams, suspensions, lotions, powders, solutions, pastes, gels, sprays, aerosols or oils. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions comprised of an sErbB3 agent adapted for rectal administration may be presented as suppositories or enemas.

Pharmaceutical compositions comprised of an sErbB3 agent adapted for nasal administration wherein the carrier is a solid include a coarse powder having a particle size for example in the range of 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions comprised of an sErbB3 agent adapted for administration by inhalation include fine particle dusts or mists which may be generated by means of various types of metered dose pressurised aerosols, nebulizers or insufflators.

Pharmaceutical compositions comprised of an sErbB3 agent adapted for vaginal administration may be presented as pessaries, tampons, creams, gels, pastes, foams or spray compositions.

Pharmaceutical compositions of dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

The compositions described herein can be formulated so as to provide quick, sustained or delayed release of the active ingredient after administration to a patient by employing any of the procedures well known in the art. In one example, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (for example liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions of embodiments of the present invention may be manufactured in a manner that is itself known, e.g., by means of conventional mixing, dissolving, granulating, dragee-making, levigating, emulsifying, encapsulating, entrapping or lyophilizing processes.

Thus, in an additional embodiment, the present invention provides a pharmaceutical composition comprising at least one agent of embodiments of the invention, optionally together with one or more pharmaceutically acceptable excipients, carriers or diluents. The pharmaceutical compositions can be included in a container, pack, or dispenser together with instructions for administration.

The pharmaceutical composition may be provided in unit dosage form, and may generally be provided in a sealed container, and may be provided as part of a kit. Such a kit may include instructions for use and a plurality of the unit dosage forms.

Dosages of the active agent of embodiments of the present invention can vary between wide limits, depending upon the disease or disorder to be treated, and the age, condition, and response of the individual to be treated. A physician will ultimately determine appropriate dosages to be used. This dosage may be repeated as often as appropriate. If side effects develop the amount and/or frequency of the dosage can be reduced in accordance with normal clinical practice.

Embodiments of the invention further provide quantitative diagnostic and pharmaceutical packs and kits comprising one or more containers filled with one or more of the ingredients of the aforementioned compositions of embodiments of the invention. Associated with such container(s) can be a notice in the form prescribed by a governmental agency regulating the manufacture, use or sale of pharmaceuticals or biological products, reflecting approval by the agency of the manufacture, use or sale of the product for human administration. Informational material can be included which is descriptive, instructional, marketing or other material that relates to the methods described herein and/or the use of the agent for the methods described herein. The kit may contain separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In various embodiments, the kit includes a plurality of individual containers, each containing one or more unit dosage forms of the agent. For example, the kit includes a plurality of syringes, ampules, foil packets, or blister packs, each containing a single unit dose of the agent. The containers of the kits can be air tight and/or waterproof. The kit optionally includes a device suitable for administration of the composition.

In a further embodiment, the present invention provides a method for the treatment of cancer in a subject, for example a human, which comprises administering to the subject a therapeutically effective amount of at least one active agent of the invention. Such agent may be in the form of a pharmaceutical composition as described herein. The method may include more than one sErbB3 agent, more than one sErbB3 isoform, as well as additional therapeutics or combinations thereof.

The present invention has been described with reference to specific details of particular embodiments thereof. It is not intended that such details be regarded as limitations upon the scope of the invention except insofar as and to the extent that they are included in the accompanying claims.

EXAMPLES

Conditioned Media from Cells Expressing p45-sErbB3 and p85-sErbB3 Inhibit HRG Activation of ErbB3. p45-sErbB3 and p85-sErbB3 are naturally occurring secreted products of the ErbB3 gene (Lee and Maihle 1998). p45-sErbB3 contains the amino-terminal 310 amino acids of ErbB3 and two unique carboxy-terminal amino acid residues. p85-sErbB3 contains the amino-terminal 519 amino acids of ErbB3 and 24 unique carboxy-terminal amino acid residues (See FIG. 1). To examine whether p45-sErbB3 and p85-sErbB3 can modulate HRG receptor activation cells stably transfected with these corresponding cDNA clones were isolated. These cells secrete p45-sErbB3 and p85-sErbB3 into the culture medium (See FIG. 2A). The conditioned medium from these cells was used as the source of p45-sErbB3 or p85-sErbB3 in a series of experiments described below.

Figure 2:
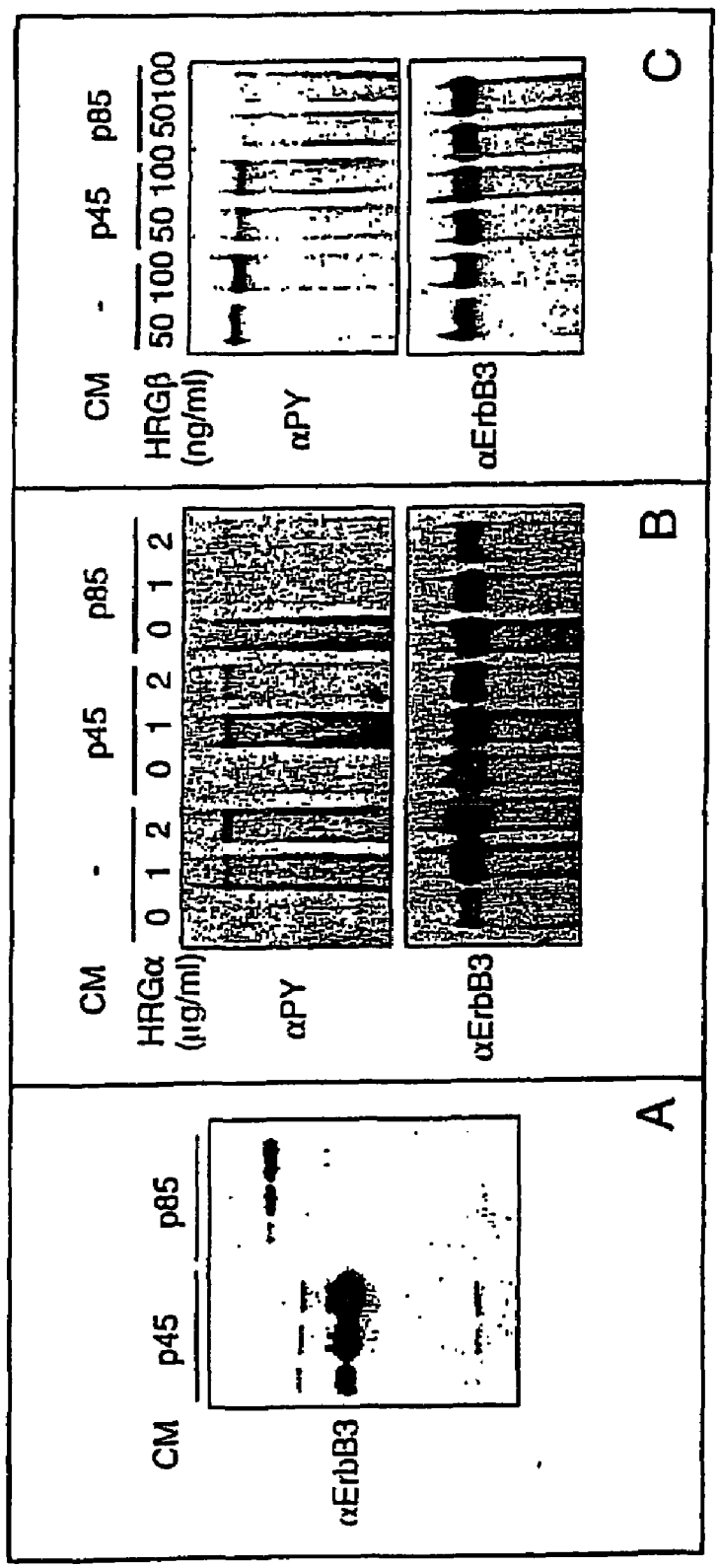
FIG. 2. demonstrates that p45-sErbB3 and p85-sErbB3 in conditioned media can block HRG-induced activation of ErbB3. (A) p45-sErbB3 and p85-sErbB3 in the concentrated conditioned media were detected by Western blotting using an anti-ErbB3 antibody recognizing the extracellular region of ErbB3. Increasing volumes (5, 10, 20 µl; left to right) of the concentrated conditioned media (×15) were loaded on an SDS-PAGE gel. (B) and (C) The Ba/F3 (ErbB2+ErbB3) cells were stimulated with HRGα (panel B) and HRGβ (panel C) with or without the concentrated conditioned media for 10 min at room temperature prior to lysis. ErbB3 was immuno-precipitated with an anti-ErbB3 antibody from equal amounts of total protein, subjected to SDS-PAGE, and analyzed by Western blotting using an anti-phosphotyrosine antibody (SPY). Filters were stripped and reprobed with anti-ErbB3 antibody recognizing the intracellular region of ErbB3.

To test the ability of p45-sErbB3 and p85-sErbB3 to modulate aspects of HRG-mediated ErbB receptor activation a clonal derivative of the Ba/F3 cell line expressing exogenous ErbB2 and ErbB3 was stimulated with HRGα EGF domain$_{77-241}$ (HRGα) and HRGβ1 EGF domain 176-246 (HRGβ) in the absence or presence of concentrated conditioned media containing p45-sErbB3 and p85-sErbB3. As shown in FIG. 2, HRGβ was at least 20-fold more effective than HRGα in stimulating ErbB3 tyrosine phosphorylation. Conditioned media containing sErbB3 inhibited HRGα-stimulated ErbB3 activation by 40% (p45-sErbB3) and 80% (p85-sErbB3) at 1 μg/ml HRGα, as determined by densitometric analysis. However, at a higher concentration (2 μg/ml), conditioned media containing p85-sErbB3 decreased activation by 30%, although inhibition by conditioned media containing p45-sErbB3 was negligible (See FIG. 2A). In the presence of conditioned medium containing either p45-sErbB3 or p85-sErbB3, ligand stimulation of ErbB3 tyrosine phosphorylation was decreased by 60% and 90%, respectively, at both 50 and 100 ng/ml HRGβ (See FIG. 2C). These data indicate that p85-sErbB3 inhibited ErbB3 phosphorylation in response to both HRGα and HRGβ more effectively than p45-sErbB3, although the concentration of p85-sErbB3 used in these studies was lower than that of p45-sErbB3 (FIG. 2A).

Purification of p85-sErbB3. p85-sErbB3 was isolated from a concentrated conditioned medium of cells stably transfected with a cDNA clone R31F encoding p85-sErbB3 and was purified in two steps. The first step was lectin affinity chromatography with a Con A column (Sigma). The bound p85-sErbB3 was washed with column buffer (10 mM Tris-HCl, pH 7.5, 150 mM NaCl, 1 mM $MnCl_2$, and 1 mM $CaCl_2$) and eluted using column buffer containing 1 M α-methyl D-mannoside, then dialyzed against 20 mM Tris-HCl, pH 7.5 overnight. The second step of purification was accomplished using a Mono Q® anion exchange chromatography column for resolution of proteins and peptides on an FPLC® system, i.e., a microprocessor controlled, solvent delivery apparatus used in purification of biologically active compounds column (Pharmacia). The bound p85-sErbB3 was eluted from the column with 0-500 mM NaCl gradient containing 20 mM Tris-HCl, pH 7.5. Samples taken from each step were subjected to SDS-PAGE in duplicate and analyzed by Coomassie staining and by Western blot using anti-ErbB3 236 antibody recognizing the extracellular domain of the ErbB3 (Lee and Maihle 1998). The final p85-sErbB3 pool was homogeneous on SDS-PAGE, and the identity of the purified protein was confirmed by Western blot analysis. Purified preparations of p85-sErbB3 were used in all subsequent experiments.

p85-sErbB3 Binds to HRG with High Affinity. Previous reports based the assignation of the subdomain boundaries for the ErbB3 extracellular domain on the subdomain boundaries of EGFR (Lee and Maihle 1998) as defined by the genomic structure of avian ErbB1(Callaghan, Antczak et al. 1993). Accordingly, p85-sErbB3 is composed of subdomains I through III and includes the first 45 amino acids of subdomain IV (aa 1-519), and a unique twenty-four amino acid sequence at the carboxy-terminus. Binding studies using heregulins indicate that subdomains I and II are required for heregulin binding (Singer, Landgraf et al. 2001). On the other hand, for EGF binding to EGFR subdomains I and III are low and high affinity binding sites, respectively (Lax, Bellot et al. 1989).

Figure 3:
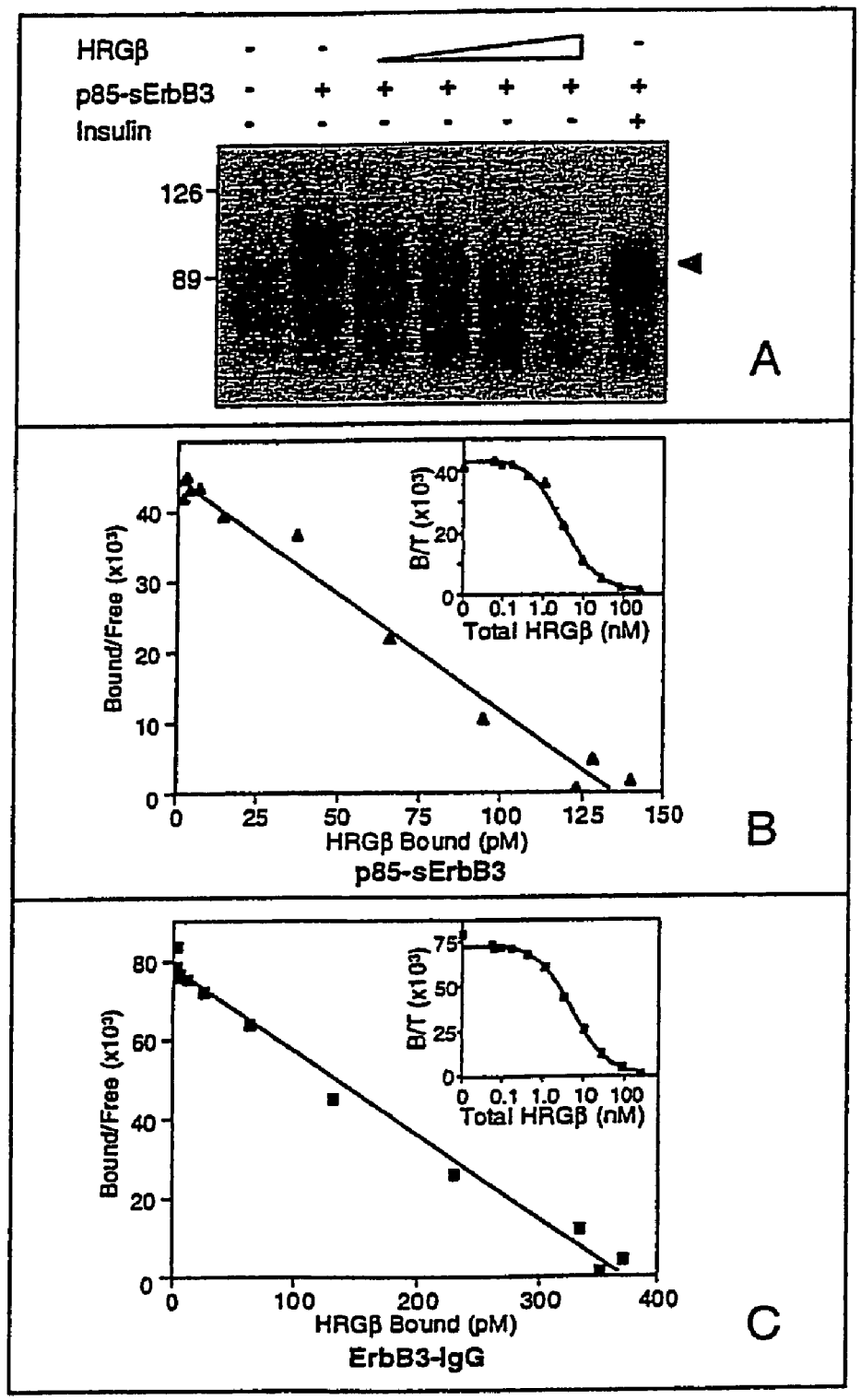
FIG. 3. demonstrates p85-sErbB3 binds to HRG. (A) HRGβ was crosslinked to p85-sErbB3 (25 nM) with $BS^3$ after incubating in the presence of 50 nM $^{125}$I-HRGβ without or with increasing concentrations (0.16, 0.32, 0.64, 1.25 µM) of unlabeled HRGβ. Insulin (1.25 µM) was used as a negative control. The arrowhead indicates a 90 kDa complex of $^{125}$I-HRGβ and p85-sErbB3. (B) and (C) Binding analysis of $^{125}$I-HRG to p85-sErbB3 and ErbB3-IgG fusion protein. Binding assays were performed in a 96-well plate format as described below in more detail in the Examples. Binding results were analyzed by using Scatchard method and by plotting the displacement of $^{125}$I-HRGβ$_{177-244}$ binding by unlabeled HRGβ$_{177-244}$ (Inset).
Figure 4:
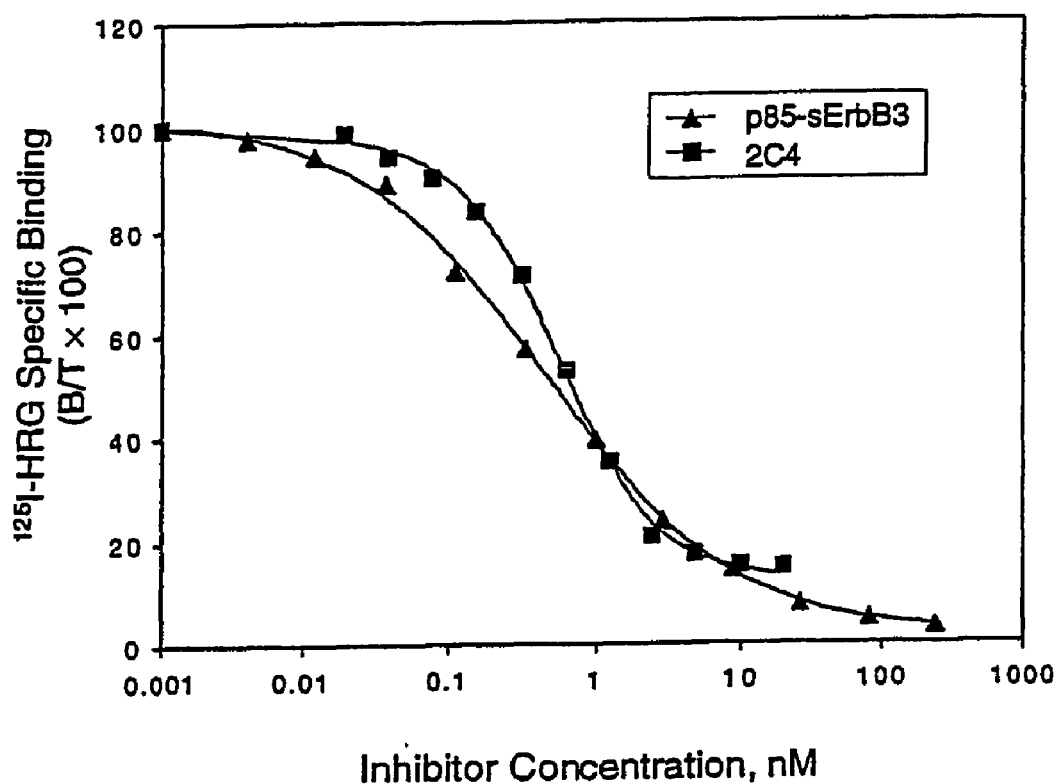
FIG. 4. is a graph showing inhibition of HRGβ binding by p85-sErbB3 and by 2C4, a monoclonal antibody specific for ErbB2. T47D cells were incubated with the indicated concentrations of p85-sErbB3 and 2C4 at room temperature for 30 min. $^{125}$I-HRGβ$_{177-244}$ (0.1 nM) was then added and binding reactions were performed as described below in more detail in the Examples. $^{125}$I-HRGβ$_{177-244}$ bound to the cell surface was measured using a gamma counter.
Figure 5:
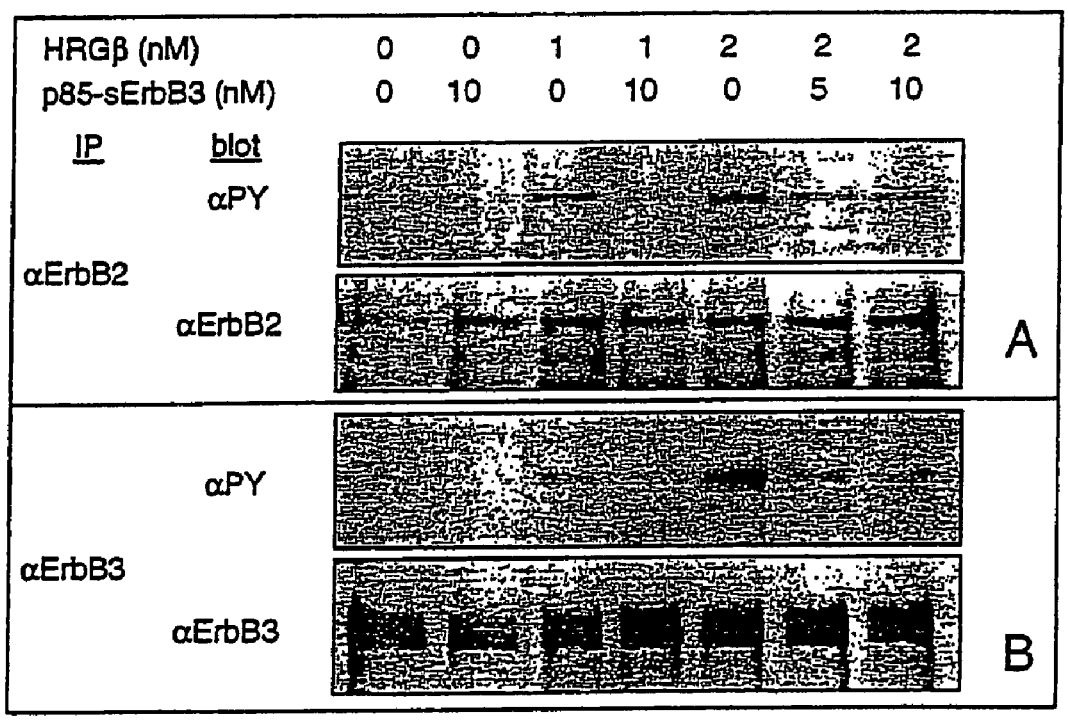
FIG. 5. demonstrates p85-sErbB3 blocks HRG-induced activation of ErbB2 and ErbB3 in the Ba/F3 (ErbB2+ErbB3) cells. Cells were untreated or stimulated with HRGβ$_{1-241}$ alone or HRGβ$_{1-241}$ plus purified p85-sErbB3 for 10 min at room temperature. Receptor phosphorylation levels and ErbB2 and ErbB3 receptor levels were determined by anti-ErbB2 (A) and anti-ErbB3 (B) immunoprecipitation followed by Western blotting as described in FIG. 2.

Direct binding between p85-sErbB3 and radiolabeled HRGβ was examined using the chemical crosslinker $BS^3$. As shown in FIG. 3A, a protein complex of 90 kDa was formed between p85-sErbB3 and $^{125}$I-HRGβ. Formation of this complex could be inhibited by addition of excess cold HRGβ but not by addition of excess insulin, indicating that p85-sErbB3 binding to HRGβ is specific and that purified preparations of p85-sErbB3 are biologically active. An analysis of $^{125}$I-HRGβ$_{177-244}$ binding to immobilized p85-sErbB3 was then performed using an ErbB3-IgG homodimer as a positive control. As shown in FIG. 3, p85-sErbB3 binds to HRGβ$_{177-244}$ with a $K_D$ of 3.0±0.2 nM. In comparison, ErbB3-IgG binds to HRGPβ$_{177-244}$ with a $K_D$ of 4.7±0.2 nM. These results demonstrate that p85-sErbB3 binds to HRGβ$_{177-244}$ with an affinity similar to that of the extracellular domain of ErbB3. The results of these two complementary experimental approaches establish the use of p85-sErbB3 to bind to HRG with an affinity equivalent to the affinity of HRG for the full-length extracellular domain of ErbB3.

p85-sErbB3 Inhibits Binding of HRG to Receptors on the Cell Surface. p85-sErbB3 effectively limits binding of heregulin to cell surface receptors in the breast carcinoma cell line T47D. This cell line expresses all four ErbB receptors at moderate levels. Cells were incubated with varying concentrations of p85-sErbB3 in the presence of $^{125}$I-labeled HRGβ$_{177-244}$. Simultaneously, a separate group of cells was incubated with $^{125}$I-HRGβ$_{177-244}$ in the presence of varying concentrations of 2C4, a monoclonal antibody specific for the ErbB2 extracellular domain (Lewis, Lofgren et al. 1996). As shown by the inhibition curves (See FIG. 4), p85-sErbB3 and 2C4 inhibit HRGβ$_{177-244}$ binding to cell surface receptors with similar $IC_{50}$ values (0.45±0.03 nM and 0.55±0.03 nM, respectively) although the mechanism of inhibition by these two molecules is distinct. Although 2C4 inhibits heregulin binding to cell surface receptors by blocking ErbB2-ErbB3 heterodimerization via binding to the ErbB2 extracellular domain (Fitzpatrick, Pisacane et al. 1998), p85-sErbB3 inhibits receptor activation and heterodimerization, at least in part, by competing for heregulin binding to the cell surface.

p85-sErbB3 Blocks HRG-Induced Activation of ErbB2, ErbB3, and ErbB4. The ability of p85-sErbB3 to modulate HRG-stimulated receptor activation in the Ba/F3 (ErbB2+ ErbB3) cell line was examined using purified p85-sErbB3. This allowed an analysis of the mechanism of p85-sErbB3 mediated inhibition in a quantitative manner. As shown in FIG. 5, when Ba/F3 (ErbB2+ErbB3) cells were treated with p85-sErbB3 at a 10-fold molar excess over HRGβ$_{1-241}$, ErbB3 phosphorylation levels were reduced to basal levels. A similar level of receptor inhibition also was apparent when either a 2.5- or 5-fold molar excess of p85-sErbB3 was used in these experiments. Exogenous addition of p85-sErbB3 also inhibited HRG-induced ErbB2 activation. p85-sErbB3 blocked HRG stimulation whether the cells were treated with the EGF-like domain of HRG (HRGα or HRGβ), as shown in FIG. 2, or with the entire HRGβ$_{1-241}$ growth factor (See FIG. 5), suggesting that inhibition by p85-sErbB3 occurs, at least in part, through a direct interaction between p85-sErbB3 and the EGF-like domain of HRG. Cells treated with the same concentration of p85-sErbB3 but not stimulated with HRG did not exhibit altered ErbB2 or ErbB3 tyrosine phosphorylation, or show any change in the level of either ErbB2 or ErbB3 expression, suggesting that p85-sErbB3 does not function as a "ligand" for these receptors.

Figure 6:
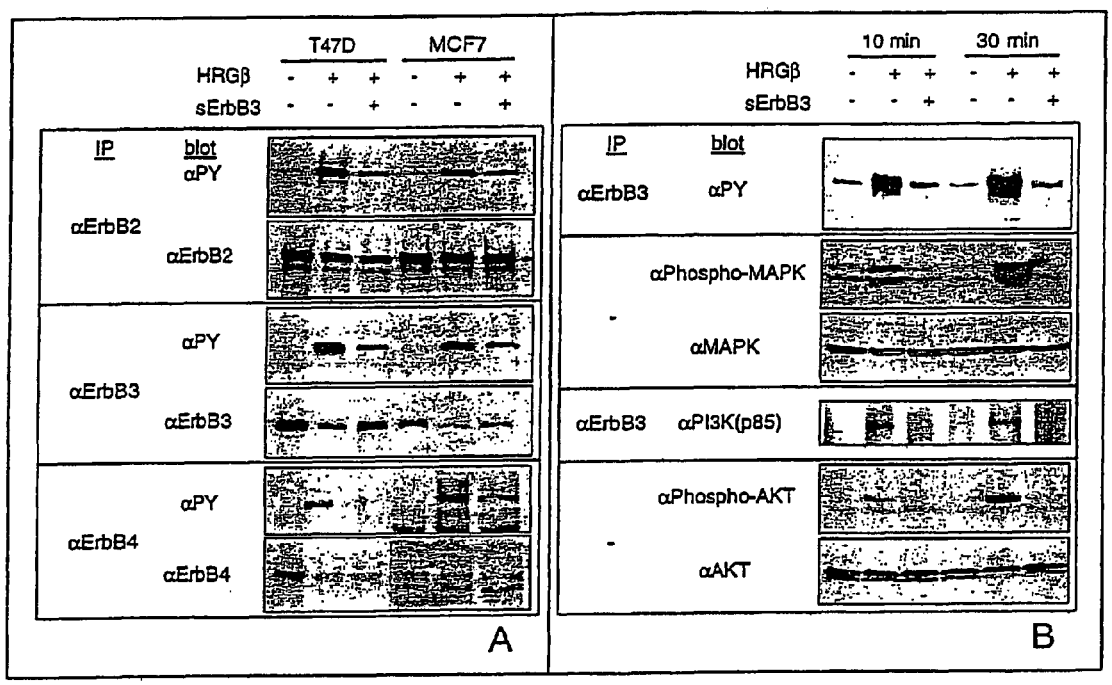
FIG. 6. demonstrates p85-sErbB3 blocks HRG-induced activation of ErbB proteins and their downstream activators MAPK, PI3K (p85), and Akt. (A) p85-sErbB3 blocks HRG-induced activation of ErbB2, ErbB3, and ErbB4 in T47D and MCF7 breast carcinoma cells. Serum-starved cells were stimulated with no HRGβ, HRGβ alone, or 6 nM HRGβ plus 36 nM p85-sErbB3 for 10 min at room temperature. Receptor phosphorylation levels and ErbB2, ErbB3, and ErbB4 receptor levels were determined by immunoprecipitation followed by Western blotting. (B) p85-sErbB3 inhibits HRG-induced association of PI3K (p85) with ErbB3 and activation of MAPK and Akt in T47D cells. Cells were treated with 1 nM HRGβ and 10 nM p85-sErbB3 for 10 min or 30 min and analyzed for activation of ErbB3. Association of PI3K (p85) with ErbB3 was analyzed by immunoprecipitation of cell lysates using an anti-ErbB3 antibody followed by Western blotting of anti-PI3K (p85) antibody. Activation of MAPK and Akt was examined by Western blotting of cell lysates using antibodies specific to phospho-MAPK and phospho-Akt.

To examine whether exogenous addition of p85-sErbB3 exerts the same inhibitory effect on endogenously expressed ErbB receptors, and to determine whether p85-sErbB3 could modulate other members of the EGF receptor family, the activity of p85-sErbB3 in two breast carcinoma cell lines, i.e., T47D and MCF7, was tested. As shown in FIG. 6A, addition of p85-sErbB3 (at a 6-fold molar excess relative to HRGβ) inhibited HRG-induced activation of ErbB2, ErbB3, and ErbB4 in both the T47D and MCF7 cell lines. In contrast, at least in these two cell lines which express low EGFR levels, EGFR phosphorylation remained at basal level in cells treated with HRGβ regardless of whether p85-sErbB3 was present or not. Similarly, EGF-induced phosphorylation of EGFR or ErbB2, or, to a lesser degree, phosphorylation of ErbB3, was not decreased by p85-sErbB3. These results demonstrate that inhibition by p85-sErbB3 is specific for HRG-induced activation of ErbB2, ErbB3, and ErbB4.

Figure 7:
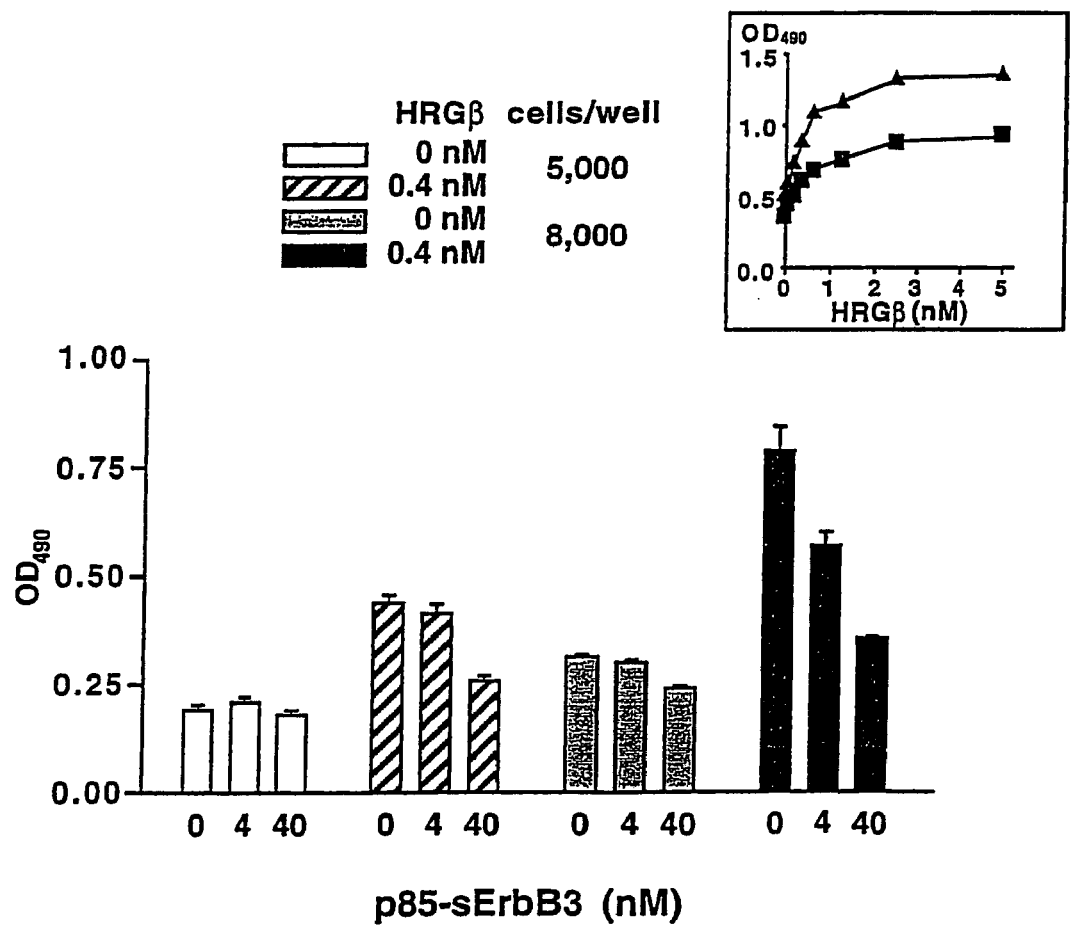
FIG. 7. demonstrates p85-sErbB3 inhibits cell growth stimulation by HRG. MCF7 cells were trypsinized, washed, and plated at a density of 5,000 (squares) or 8,000 cells/well (triangles) in 96-well plates with increasing concentrations of HRGβ in serum-free medium and growth was measured after 3 days (inset). MCF7 cells were trypsinized, washed, incubated with p85-sErbB3 for 30 min, and plated with or without 0.4 nM HRGβ in serum-free medium. At 40 nM (a 100-fold molar excess to HRGβ) in the presence of HRGβ, p85-sErbB3 inhibited cell growth by 75% and 90%, at densities of 5,000 and 8,000 cells/well, respectively, whereas the same concentration of p85-sErbB3 did not affect cell growth in the absence of HRGβ. The data presented are the mean±standard deviation of six replicates. This experiment was repeated three times and the results shown represent all three trials.
Figure 8:
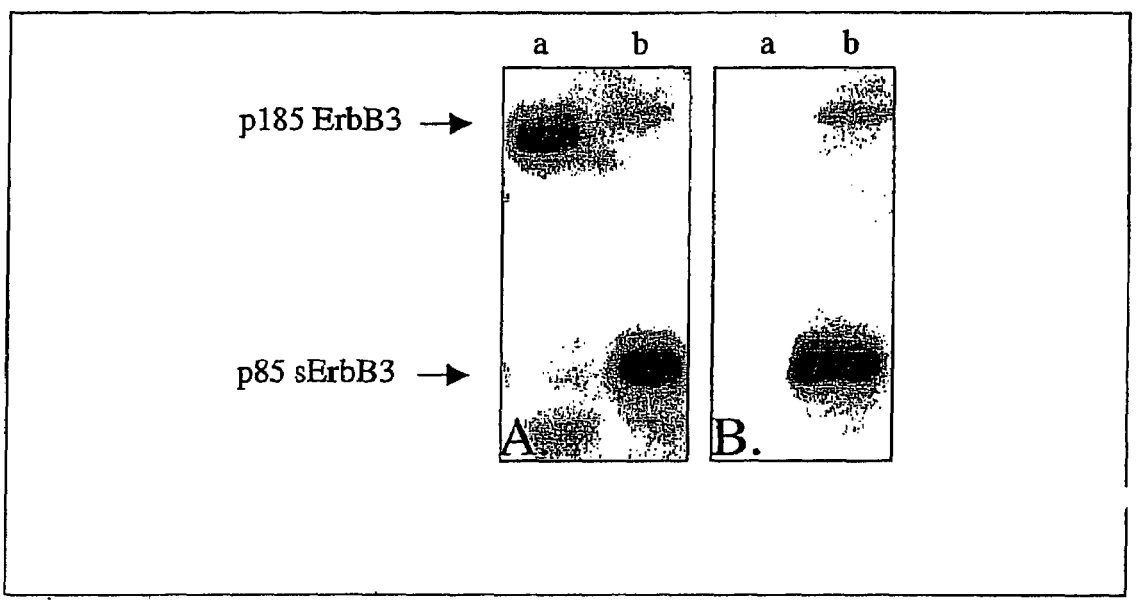
FIG. 8 is an immunoblot demonstrating specificity of the p85-sErbB3 antibody.

It is notable that in T47D cells, a decrease in ErbB2, ErbB3, and ErbB4 protein levels following HRG stimulation was observed. In MCF7 cells a decrease in ErbB3 levels also was apparent when HRG was added to the culture medium (See FIG. 6A). It has been reported that the polyclonal ErbB3 antibody specific to the carboxy-terminal 17 aa used in this study preferentially recognizes non-phosphorylated ErbB3 on Western blots (Vartanian, Goodearl et al. 1997). Thus, when T47D or MCF7 cells are stimulated with HRG, a significant fraction of ErbB3 is phosphorylated, and, therefore, undetectable with this particular ErbB3 antibody. The anti-ErbB anitbodies used in these experiments recognize the carboxy-terminal 17 aa (ErbB3) and 18 aa (ErbB2 and ErbB4) sequences of these receptors. Each of these sequences contains one tyrosine residue. Immunoblot detection by the anti-ErbB2 and ErbB4 antibodies used in this study, therefore, may reflect either the elvel of receptor expression or the unphosphorylated fraction of these receptors.

p85-sErbB3 Inhibits Activation of Downstream Effectors of HRG. HRG-stimulated activation of ErbB2, ErbB3, and ErbB4 leads to activation of two major signal transduction pathways: the PI3K pathway and the MAPK pathway (Wallasch, Weiss et al. 1995). To test whether p85-sErbB3 could inhibit activation of these two downstream effector pathways in T47D cells, activation of MAPK and Akt was examined by analyzing the phosphorylation levels of these proteins, and the ability of p85 phosphatidylinositide 3-kinase ("PI3K" to interact with ErbB3 following HRGβ treatment. In the presence of p85-sErbB3 (10-fold molar excess relative to HRGβ), tyrosine phosphorylation of ErbB3 was reduced to basal levels. In the same cell population, addition of exogenous p85-sErbB3 abrogated the phosphorylation of both MAPK and Akt as determined by Western blot analysis, and inhibited ErbB3's association with p85 PI3K (See FIG. 6B). These results further demonstrate the p85-sErbB3 can inhibit the activation of ErbB2, ErbB3, and ErbB4, and this inhibition affects the activation of downstream signaling molecules such as MAPK, Akt, and PI3K.

p85-sErbB3 Inhibits HRG-Stimulated Cell Growth. Inhibition of HRG-induced phosphorylation of ErbB receptors by p85-sErbB3 correlates with the modulation of HRG's biological effects. Specifically, a cell growth assay using MCF7 cells stimulated with HRGβ was performed and showed that, within the concentration range tested, growth of this cell line was dose-dependent (see FIG. 7). It was observed that ant a concentration of 0.4 nM HRGβ the cell growth rate was half of the rate observed at saturating levels of HRGβ. In cell cultures grown in the presence of 0.4 nM HRGβ and p85-sErbB3 (a 100-fold molar excess relative to HRGβ), p85-sErbB3 inhibited cell growth by 75% and 90%, at densities of 5,000 and 8,000 cells/well, respectively, whereas the same concentration of p85-sErbB3 did not affect cell growth in the absence of HRGβ (See FIG. 7). Thus, the present invention discloses the use of p85-sErbB3 as a potent inhibitor of HRG-dependent breast carcinoma cell growth in vitro.

p85-sErbB3 antibodies. Soluble ErbB3 antibodies are directed to the unique C-terminal regions. Rabbit polyclonal antibodies specific for p85-sErbB3 were generated using a 23 aa polypeptide from the unique carboxy-terminal region (amino acids 540-562 of SEQ ID NO: 2: Ser Lys Gly Ser Gln Ser Arg Met Gly Gly Gly Gly Ala Leu Gln Trp Asn Cys Ser Gly Gly Ile Gln) and methods known in the art. Two rabbits were used; 10 ml preimmunize serum were collected from both rabbits, and both rabbits elicited high titer antibody production in response to immunization with the 23-mer carboxy-terminus of p85 sErbB3 as determined using enzyme-linked immunosorbent assays [ELISA] using the immunizing peptide as substrate; data not shown. Crude antiserum (IgG preps from whole serum) from both rabbits specifically detect an 85 kDa apparent molecular weight protein, that comigrates with an p85 kDa species detected by an anti-ErbB3 (ECD) antibody (FIG. 8); neither anti-sErbB3 antibody shows significant cross reactivity with other proteins (including p185 ErbB3) as demonstrated by immunoblot analysis. These same antibody preparations were used to stain approximately 50 breast tumors, using either preimmune serum or peptide competition controls, labeling was specific for p85-sErbB3 in both normal and malignant breast tissues. Results in both normal and malignant breast tissue indicate a moderate to high level of sErbB3 expression, restricted mainly to parenchymal epithelial cells, with no evidence of stromal staining. Importantly, the specificity of this staining pattern has been demonstrated through the use of both pre-immune and peptide competition controls (data not shown).

p85-sErbB3 expression in tissues. Immunohistochemistry analysis using the p85-sErbB3 specific antibody, and using both pre-immune and peptide competition controls, showed p85-sErbB3 expression in most tissues or organs, including the esophagus, stomach, liver, gall bladder, small bowel, ureter, colon, thyroid gland, tonsils, lymph nodes, spleen, thymus, skeletal muscle, bronchioles, heart (epicardium and myocardium), hippocampus, head and neck, kidney, bladder, pancreas, adrenal gland, lung, skin, breast, ovary, uterus (cervix and endometrium), fallopian tube, placenta, prostate gland, brain, intestine, or testis. (data not shown).

We claim:

1. An isolated antibody that specifically recognizes an sErbB3 polypeptide, wherein the antibody binds a unique carboxy terminal region of the sErbB3 polypeptide comprising amino acid residues 539-562 of SEQ ID NO: 2, amino acid residues 330-331 of SEQ ID NO: 4, amino acid residues 494-534 of SEQ ID NO: 6, or amino acid residues 371-400 of SEQ ID NO: 8.

2. The antibody of claim 1, wherein said antibody is a monoclonal antibody.

3. The antibody of claim 1, wherein said antibody is a polyclonal antibody.

4. The antibody of claim 1, wherein said antibody is a humanized antibody.

5. The antibody of claim 1, wherein said antibody is a human antibody.

6. The antibody of claim 1, wherein said antibody is conjugated to a therapeutic moiety or a detectable moiety selected from the group consisting of an enzyme, prosthetic group, fluorescent material, luminescent material, bioluminescent material, radioactive nuclide, positron emitting metal, and nonradioactive paramagnetic metal ion.

7. A pharmaceutical composition comprising an sErbB3 antibody and a pharmaceutically acceptable carrier, wherein said sErbB3 antibody binds a unique carboxy terminal region of the sErbB3 polypeptide comprising amino acid residues 539-562 of SEQ ID NO: 2, amino acid residues 330-331 of SEQ ID NO: 4, amino acid residues 494-534 of SEQ ID NO: 6, or amino acid residues 371-400 of SEQ ID NO: 8.

8. The composition of claim 7 wherein said sErbB3 antibody is a monoclonal antibody.

9. A kit comprising an sErbB3 antibody and at least one informational material, wherein said sErbB3 antibody binds a unique carboxy terminal region of the sErbB3 polypeptide comprising amino acid residues 539-562 of SEQ ID NO: 2, amino acid residues 330-331 of SEQ ID NO: 4, amino acid residues 494-534 of SEQ ID NO: 6, or amino acid residues 371-400 of SEQ ID NO: 8.

* * * * *

SEQUENCE LISTING

```
<160> NUMBER OF SEQ ID NOS: 8

<210> SEQ ID NO 1
<211> LENGTH: 1800
<212> TYPE: DNA
<213> ORGANISM: Homo sapiens
<220> FEATURE:
<221> NAME/KEY: CDS
<222> LOCATION: (61)..(1746)

<400> SEQUENCE: 1 cgggccccc  ctcgaggtcg  ggccggactt  ggctgggctc  ccttcacccct  ctgcggagtc        60 atg agg gcg aac gac gct ctg cag gtg ctg ggc ttg ctt ttc agc ctg              108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act              156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca              204
Leu Asn Gly Leu Ser Val Thr Gly Asp Ala Glu Asn Gln Tyr Gln Thr
        35                  40                  45
```

-continued

| | |
|---|---|
| ctg tac aag ctc tac gag agg tgt gag gtg gtg atg ggg aac ctt gag<br>Leu Tyr Lys Leu Tyr Glu Arg Cys Glu Val Val Met Gly Asn Leu Glu<br>50                        55                      60 | 252 |
| att gtg ctc acg gga cac aat gcc gac ctc tcc ttc ctg cag tgg att<br>Ile Val Leu Thr Gly His Asn Ala Asp Leu Ser Phe Leu Gln Trp Ile<br>65                     70                   75                 80 | 300 |
| cga gaa gtg aca ggc tat gtc ctc gtg gcc atg aat gaa ttc tct act<br>Arg Glu Val Thr Gly Tyr Val Leu Val Ala Met Asn Glu Phe Ser Thr<br>                  85                   90                    95 | 348 |
| cta cca ttg ccc aac ctc cgc gtg gtg cga ggg acc cag gtc tac gat<br>Leu Pro Leu Pro Asn Leu Arg Val Val Arg Gly Thr Gln Val Tyr Asp<br>100                      105                   110 | 396 |
| ggg aag ttt gcc atc ttc gtc atg ttg aac tat aac acc aac tcc agc<br>Gly Lys Phe Ala Ile Phe Val Met Leu Asn Tyr Asn Thr Asn Ser Ser<br>        115                   120                   125 | 444 |
| cac gct ctg cgc cag ctc cgc ttg act cag ctc acc gag att ctg tca<br>His Ala Leu Arg Gln Leu Arg Leu Thr Gln Leu Thr Glu Ile Leu Ser<br>130                      135                   140 | 492 |
| ggg ggt gtt tat att gag aag aac gat aag ctt tgt cac atg gac aca<br>Gly Gly Val Tyr Ile Glu Lys Asn Asp Lys Leu Cys His Met Asp Thr<br>145                     150                  155                    160 | 540 |
| att gac tgg agg gac atc gtg agg gac cga gat gct gag ata gtg gtg<br>Ile Asp Trp Arg Asp Ile Val Arg Asp Arg Asp Ala Glu Ile Val Val<br>                  165                   170                   175 | 588 |
| aag gac aat ggc aga agc tgt ccc ccc tgt cat gag gtt tgc aag ggg<br>Lys Asp Asn Gly Arg Ser Cys Pro Pro Cys His Glu Val Cys Lys Gly<br>180                      185                   190 | 636 |
| cga tgc tgg ggt cct gga tca gaa gac tgc cag aca ttg acc aag acc<br>Arg Cys Trp Gly Pro Gly Ser Glu Asp Cys Gln Thr Leu Thr Lys Thr<br>                  195                   200                   205 | 684 |
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn<br>210                      215                   220 | 732 |
| cag tgc tgc cat gat gag tgt gcc ggg ggc tgc tca ggc cct cag gac<br>Gln Cys Cys His Asp Glu Cys Ala Gly Gly Cys Ser Gly Pro Gln Asp<br>225                      230                   235                    240 | 780 |
| aca gac tgc ttt gcc tgc cgg cac ttc aat gac agt gga gcc tgt gta<br>Thr Asp Cys Phe Ala Cys Arg His Phe Asn Asp Ser Gly Ala Cys Val<br>                  245                   250                   255 | 828 |
| cct cgc tgt cca cag cct ctt gtc tac aac aag cta act ttc cag ctg<br>Pro Arg Cys Pro Gln Pro Leu Val Tyr Asn Lys Leu Thr Phe Gln Leu<br>260                      265                   270 | 876 |
| gaa ccc aat ccc cac acc aag tat cag tat gga gga gtt tgt gta gcc<br>Glu Pro Asn Pro His Thr Lys Tyr Gln Tyr Gly Gly Val Cys Val Ala<br>                275                   280                   285 | 924 |
| agc tgt ccc cat aac ttt gtg gtg gat caa aca tcc tgt gtc agg gcc<br>Ser Cys Pro His Asn Phe Val Val Asp Gln Thr Ser Cys Val Arg Ala<br>290                      295                   300 | 972 |
| tgt cct cct gac aag atg gaa gta gat aaa aat ggg ctc aag atg tgt<br>Cys Pro Pro Asp Lys Met Glu Val Asp Lys Asn Gly Leu Lys Met Cys<br>305                      310                   315                    320 | 1020 |
| gag cct tgt ggg gga cta tgt ccc aaa gcc tgt gag gga aca ggc tct<br>Glu Pro Cys Gly Gly Leu Cys Pro Lys Ala Cys Glu Gly Thr Gly Ser<br>                  325                   330                   335 | 1068 |
| ggg agc cgc ttc cag act gtg gac tcg agc aac att gat gga ttt gtg<br>Gly Ser Arg Phe Gln Thr Val Asp Ser Ser Asn Ile Asp Gly Phe Val<br>                  340                   345                   350 | 1116 |
| aac tgc acc aag atc ctg ggc aac ctg gac ttt ctg atc acc ggc ctc<br>Asn Cys Thr Lys Ile Leu Gly Asn Leu Asp Phe Leu Ile Thr Gly Leu | 1164 |

-continued

```
                    355                 360                 365
aat gga gac ccc tgg cac aag atc cct gcc ctg gac cca gag aag ctc        1212
Asn Gly Asp Pro Trp His Lys Ile Pro Ala Leu Asp Pro Glu Lys Leu
        370                 375                 380 aat gtc ttc cgg aca gta cgg gag atc aca ggt tac ctg aac atc cag        1260
Asn Val Phe Arg Thr Val Arg Glu Ile Thr Gly Tyr Leu Asn Ile Gln
385                 390                 395                 400 tcc tgg ccg ccc cac atg cac aac ttc agt gtt ttt tcc aat ttg aca        1308
Ser Trp Pro Pro His Met His Asn Phe Ser Val Phe Ser Asn Leu Thr
                405                 410                 415 acc att gga ggc aga agc ctc tac aac cgg ggc ttc tca ttg ttg atc        1356
Thr Ile Gly Gly Arg Ser Leu Tyr Asn Arg Gly Phe Ser Leu Leu Ile
            420                 425                 430 atg aag aac ttg aat gtc aca tct ctg ggc ttc cga tcc ctg aag gaa        1404
Met Lys Asn Leu Asn Val Thr Ser Leu Gly Phe Arg Ser Leu Lys Glu
        435                 440                 445 att agt gct ggg cgt atc tat ata agt gcc aat agg cag ctc tgc tac        1452
Ile Ser Ala Gly Arg Ile Tyr Ile Ser Ala Asn Arg Gln Leu Cys Tyr
    450                 455                 460 cac cac tct ttg aac tgg acc aag gtg ctt cgg ggg cct acg gaa gag        1500
His His Ser Leu Asn Trp Thr Lys Val Leu Arg Gly Pro Thr Glu Glu
465                 470                 475                 480 cga cta gac atc aag cat aat cgg ccg cgc aga gac tgc gtg gca gag        1548
Arg Leu Asp Ile Lys His Asn Arg Pro Arg Arg Asp Cys Val Ala Glu
                485                 490                 495 ggc aaa gtg tgt gac cca ctg tgc tcc tct ggg gga tgc tgg ggc cca        1596
Gly Lys Val Cys Asp Pro Leu Cys Ser Ser Gly Gly Cys Trp Gly Pro
            500                 505                 510 ggc cct ggt cag tgc ttg tcc tgt cga aat tat agc cga gga ggt gtc        1644
Gly Pro Gly Gln Cys Leu Ser Cys Arg Asn Tyr Ser Arg Gly Gly Val
        515                 520                 525 tgt gtg acc cac tgc aac ttt ttg aat ggg tac agt aag ggg agc cag        1692
Cys Val Thr His Cys Asn Phe Leu Asn Gly Tyr Ser Lys Gly Ser Gln
    530                 535                 540 tca agg atg ggt ggg ggt ggg gcc ctg caa tgg aac tgt tca ggt ggc        1740
Ser Arg Met Gly Gly Gly Gly Ala Leu Gln Trp Asn Cys Ser Gly Gly
545                 550                 555                 560 ata caa taaaagtctt tagacaaaaa aaaaaaaaaa aaaaaaaaaa aaaaaaaaaa         1796
Ile Gln aaaa                                                                   1800
```

<210> SEQ ID NO 2
<211> LENGTH: 562
<212> TYPE: PRT
<213> ORGANISM: Homo sapiens

<400> SEQUENCE: 2

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr

```
                 85                  90                  95
Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510
```

```
Gly Pro Gly Gln Cys Leu Ser Cys Arg Asn Tyr Ser Arg Gly Gly Val
            515                 520                 525

Cys Val Thr His Cys Asn Phe Leu Asn Gly Tyr Ser Lys Gly Ser Gln
        530                 535                 540

Ser Arg Met Gly Gly Gly Ala Leu Gln Trp Asn Cys Ser Gly Gly
545                 550                 555                 560

Ile Gln

<210> SEQ ID NO 3
<211> LENGTH: 1420
<212> TYPE: DNA
<213> ORGANISM: Homo sapiens
<220> FEATURE:
<221> NAME/KEY: CDS
<222> LOCATION: (61)..(1053)

<400> SEQUENCE: 3
```

| | |
|---|---:|
| cgggccccc ctcgaggtcg ggccggactt ggctgggctc ccttcaccct ctgcggagtc | 60 |

| | | |
|---|---|---:|
| atg agg gcg aac gac gct ctg cag gtg ctg ggc ttg ctt ttc agc ctg<br>Met Arg Ala Asn Asp Ala Leu Gln Val Leu Gly Leu Leu Phe Ser Leu<br>1               5                   10                  15 | | 108 |
| gcc cgg ggc tcc gag gtg ggc aac tct cag gca gtg tgt cct ggg act<br>Ala Arg Gly Ser Glu Val Gly Asn Ser Gln Ala Val Cys Pro Gly Thr<br>            20                  25                  30 | | 156 |
| ctg aat ggc ctg agt gtg acc ggc gat gct gag aac caa tac cag aca<br>Leu Asn Gly Leu Ser Val Thr Gly Asp Ala Glu Asn Gln Tyr Gln Thr<br>        35                  40                  45 | | 204 |
| ctg tac aag ctc tac gag agg tgt gag gtg gtg atg ggg aac ctt gag<br>Leu Tyr Lys Leu Tyr Glu Arg Cys Glu Val Val Met Gly Asn Leu Glu<br>    50                  55                  60 | | 252 |
| att gtg ctc acg gga cac aat gcc gac ctc tcc ttc ctg cag tgg att<br>Ile Val Leu Thr Gly His Asn Ala Asp Leu Ser Phe Leu Gln Trp Ile<br>65                  70                  75                  80 | | 300 |
| cga gaa gtg aca ggc tat gtc ctc gtg gcc atg aat gaa ttc tct act<br>Arg Glu Val Thr Gly Tyr Val Leu Val Ala Met Asn Glu Phe Ser Thr<br>                85                  90                  95 | | 348 |
| cta cca ttg ccc aac ctc cgc gtg gtg cga ggg acc cag gtc tac gat<br>Leu Pro Leu Pro Asn Leu Arg Val Val Arg Gly Thr Gln Val Tyr Asp<br>            100                 105                 110 | | 396 |
| ggg aag ttt gcc atc ttc gtc atg ttg aac tat aac acc aac tcc agc<br>Gly Lys Phe Ala Ile Phe Val Met Leu Asn Tyr Asn Thr Asn Ser Ser<br>        115                 120                 125 | | 444 |
| cac gct ctg cgc cag ctc cgc ttg act cag ctc acc gag att ctg tca<br>His Ala Leu Arg Gln Leu Arg Leu Thr Gln Leu Thr Glu Ile Leu Ser<br>    130                 135                 140 | | 492 |
| ggg ggt gtt tat att gag aag aac gat aag ctt tgt cac atg gac aca<br>Gly Gly Val Tyr Ile Glu Lys Asn Asp Lys Leu Cys His Met Asp Thr<br>145                 150                 155                 160 | | 540 |
| att gac tgg agg gac atc gtg agg gac cga gat gct gag ata gtg gtg<br>Ile Asp Trp Arg Asp Ile Val Arg Asp Arg Asp Ala Glu Ile Val Val<br>                165                 170                 175 | | 588 |
| aag gac aat ggc aga agc tgt ccc ccc tgt cat gag gtt tgc aag ggg<br>Lys Asp Asn Gly Arg Ser Cys Pro Pro Cys His Glu Val Cys Lys Gly<br>            180                 185                 190 | | 636 |
| cga tgc tgg ggt cct gga tca gaa gac tgc cag aca ttg acc aag acc<br>Arg Cys Trp Gly Pro Gly Ser Glu Asp Cys Gln Thr Leu Thr Lys Thr<br>        195                 200                 205 | | 684 |
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn | | 732 |

-continued

```
                210                 215                 220
cag tgc tgc cat gat gag tgt gcc ggg ggc tgc tca ggc cct cag gac       780
Gln Cys Cys His Asp Glu Cys Ala Gly Gly Cys Ser Gly Pro Gln Asp
225                 230                 235                 240 aca gac tgc ttt gcc tgc cgg cac ttc aat gac agt gga gcc tgt gta       828
Thr Asp Cys Phe Ala Cys Arg His Phe Asn Asp Ser Gly Ala Cys Val
                245                 250                 255 cct cgc tgt cca cag cct ctt gtc tac aac aag cta act ttc cag ctg       876
Pro Arg Cys Pro Gln Pro Leu Val Tyr Asn Lys Leu Thr Phe Gln Leu
        260                 265                 270 gaa ccc aat ccc cac acc aag tat cag tat gga gga gtt tgt gta gcc       924
Glu Pro Asn Pro His Thr Lys Tyr Gln Tyr Gly Gly Val Cys Val Ala
    275                 280                 285 agc tgt ccc cat aac ttt gtg gtg gat caa aca tcc tgt gtc agg gcc       972
Ser Cys Pro His Asn Phe Val Val Asp Gln Thr Ser Cys Val Arg Ala
290                 295                 300 tgt cct cct gac aag atg gaa gta gat aaa aat ggg ctc aag atg tgt      1020
Cys Pro Pro Asp Lys Met Glu Val Asp Lys Asn Gly Leu Lys Met Cys
305                 310                 315                 320 gag cct tgt ggg gga cta tgt ccc aaa ggt ggg taggagatgg taagaagttg    1073
Glu Pro Cys Gly Gly Leu Cys Pro Lys Gly Gly
                325                 330 taaagagaca gcctttcctc tgagcctgcg cagaccaccc ccactgaacc tctcttacat    1133
ttgcagcctg tgagggaaca ggtctggga gccgcttcca gactgtggac tcgagcaaca    1193
ttgatggatt tgtgaactgc accaagatcc tgggcaacct ggactttctg atcaccggcc    1253
tcaatgggtt agagatcctg ccttccctcc ttagacccca gcccacgcac ccctcacagt    1313
tcatttcatt ggccaaaact ttcctatgtg gagctgacta ggaatcaaag tcataaaatt    1373
ctagcctgtt acaaaggaaa aaaaaaaaaa aaaaaaaaa aaaaaa                   1420

<210> SEQ ID NO 4
<211> LENGTH: 331
<212> TYPE: PRT
<213> ORGANISM: Homo sapiens

<400> SEQUENCE: 4

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160
```

-continued

```
Ile Asp Trp Arg Asp Ile Val Arg Asp Arg Asp Ala Glu Ile Val Val
            165                 170                 175
Lys Asp Asn Gly Arg Ser Cys Pro Cys His Glu Val Cys Lys Gly
            180                 185                 190
Arg Cys Trp Gly Pro Gly Ser Glu Asp Cys Gln Thr Leu Thr Lys Thr
        195                 200                 205
Ile Cys Ala Pro Gln Cys Asn Gly His Cys Phe Gly Pro Asn Pro Asn
    210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Gly Gly
                325                 330

<210> SEQ ID NO 5
<211> LENGTH: 2005
<212> TYPE: DNA
<213> ORGANISM: Homo sapiens
<220> FEATURE:
<221> NAME/KEY: CDS
<222> LOCATION: (61)..(1662)

<400> SEQUENCE: 5 cgggccccc ctcgaggtcg ggccggactt ggctgggctc ccttcaccct ctgcggagtc       60 atg agg gcg aac gac gct ctg cag gtg ctg ggc ttg ctt ttc agc ctg      108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act      156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca      204
Leu Asn Gly Leu Ser Val Thr Gly Asp Ala Glu Asn Gln Tyr Gln Thr
        35                  40                  45 ctg tac aag ctc tac gag agg tgt gag gtg gtg atg ggg aac ctt gag      252
Leu Tyr Lys Leu Tyr Glu Arg Cys Glu Val Val Met Gly Asn Leu Glu
    50                  55                  60 att gtg ctc acg gga cac aat gcc gac ctc tcc ttc ctg cag tgg att      300
Ile Val Leu Thr Gly His Asn Ala Asp Leu Ser Phe Leu Gln Trp Ile
65                  70                  75                  80 cga gaa gtg aca ggc tat gtc ctc gtg gcc atg aat gaa ttc tct act      348
Arg Glu Val Thr Gly Tyr Val Leu Val Ala Met Asn Glu Phe Ser Thr
                85                  90                  95 cta cca ttg ccc aac ctc cgc gtg gtg cga ggg acc cag gtc tac gat      396
Leu Pro Leu Pro Asn Leu Arg Val Val Arg Gly Thr Gln Val Tyr Asp
            100                 105                 110 ggg aag ttt gcc atc ttc gtc atg ttg aac tat aac acc aac tcc agc      444
Gly Lys Phe Ala Ile Phe Val Met Leu Asn Tyr Asn Thr Asn Ser Ser
        115                 120                 125
```

| | | |
|---|---|---|
| cac gct ctg cgc cag ctc cgc ttg act cag ctc acc gag att ctg tca<br>His Ala Leu Arg Gln Leu Arg Leu Thr Gln Leu Thr Glu Ile Leu Ser<br>130                   135                   140 | | 492 |
| ggg ggt gtt tat att gag aag aac gat aag ctt tgt cac atg gac aca<br>Gly Gly Val Tyr Ile Glu Lys Asn Asp Lys Leu Cys His Met Asp Thr<br>145                   150                   155                   160 | | 540 |
| att gac tgg agg gac atc gtg agg gac cga gat gct gag ata gtg gtg<br>Ile Asp Trp Arg Asp Ile Val Arg Asp Arg Asp Ala Glu Ile Val Val<br>                   165                   170                   175 | | 588 |
| aag gac aat ggc aga agc tgt ccc ccc tgt cat gag gtt tgc aag ggg<br>Lys Asp Asn Gly Arg Ser Cys Pro Pro Cys His Glu Val Cys Lys Gly<br>                   180                   185                   190 | | 636 |
| cga tgc tgg ggt cct gga tca gaa gac tgc cag aca ttg acc aag acc<br>Arg Cys Trp Gly Pro Gly Ser Glu Asp Cys Gln Thr Leu Thr Lys Thr<br>                   195                   200                   205 | | 684 |
| atc tgt gct cct cag tgt aat ggt cac tgc ttt ggg ccc aac ccc aac<br>Ile Cys Ala Pro Gln Cys Asn Gly His Cys Phe Gly Pro Asn Pro Asn<br>210                   215                   220 | | 732 |
| cag tgc tgc cat gat gag tgt gcc ggg ggc tgc tca ggc cct cag gac<br>Gln Cys Cys His Asp Glu Cys Ala Gly Gly Cys Ser Gly Pro Gln Asp<br>225                   230                   235                   240 | | 780 |
| aca gac tgc ttt gcc tgc cgg cac ttc aat gac agt gga gcc tgt gta<br>Thr Asp Cys Phe Ala Cys Arg His Phe Asn Asp Ser Gly Ala Cys Val<br>                   245                   250                   255 | | 828 |
| cct cgc tgt cca cag cct ctt gtc tac aac aag cta act ttc cag ctg<br>Pro Arg Cys Pro Gln Pro Leu Val Tyr Asn Lys Leu Thr Phe Gln Leu<br>                   260                   265                   270 | | 876 |
| gaa ccc aat ccc cac acc aag tat cag tat gga gga gtt tgt gta gcc<br>Glu Pro Asn Pro His Thr Lys Tyr Gln Tyr Gly Gly Val Cys Val Ala<br>                   275                   280                   285 | | 924 |
| agc tgt ccc cat aac ttt gtg gtg gat caa aca tcc tgt gtc agg gcc<br>Ser Cys Pro His Asn Phe Val Val Asp Gln Thr Ser Cys Val Arg Ala<br>                   290                   295                   300 | | 972 |
| tgt cct cct gac aag atg gaa gta gat aaa aat ggg ctc aag atg tgt<br>Cys Pro Pro Asp Lys Met Glu Val Asp Lys Asn Gly Leu Lys Met Cys<br>305                   310                   315                   320 | | 1020 |
| gag cct tgt ggg gga cta tgt ccc aaa gcc tgt gag gga aca ggc tct<br>Glu Pro Cys Gly Gly Leu Cys Pro Lys Ala Cys Glu Gly Thr Gly Ser<br>                   325                   330                   335 | | 1068 |
| ggg agc cgc ttc cag act gtg gac tcg agc aac att gat gga ttt gtg<br>Gly Ser Arg Phe Gln Thr Val Asp Ser Ser Asn Ile Asp Gly Phe Val<br>                   340                   345                   350 | | 1116 |
| aac tgc acc aag atc ctg ggc aac ctg gac ttt ctg atc acc ggc ctc<br>Asn Cys Thr Lys Ile Leu Gly Asn Leu Asp Phe Leu Ile Thr Gly Leu<br>                   355                   360                   365 | | 1164 |
| aat gga gac ccc tgg cac aag atc cct gcc ctg gac cca gag aag ctc<br>Asn Gly Asp Pro Trp His Lys Ile Pro Ala Leu Asp Pro Glu Lys Leu<br>370                   375                   380 | | 1212 |
| aat gtc ttc cgg aca gta cgg gag atc aca ggt tac ctg aac atc cag<br>Asn Val Phe Arg Thr Val Arg Glu Ile Thr Gly Tyr Leu Asn Ile Gln<br>385                   390                   395                   400 | | 1260 |
| tcc tgg ccg ccc cac atg cac aac ttc agt gtt ttt tcc aat ttg aca<br>Ser Trp Pro Pro His Met His Asn Phe Ser Val Phe Ser Asn Leu Thr<br>                   405                   410                   415 | | 1308 |
| acc att gga ggc aga agc ctc tac aac cgg ggc ttc tca ttg ttg atc<br>Thr Ile Gly Gly Arg Ser Leu Tyr Asn Arg Gly Phe Ser Leu Leu Ile<br>                   420                   425                   430 | | 1356 |
| atg aag aac ttg aat gtc aca tct ctg ggc ttc cga tcc ctg aag gaa<br>Met Lys Asn Leu Asn Val Thr Ser Leu Gly Phe Arg Ser Leu Lys Glu<br>                   435                   440                   445 | | 1404 |

-continued

```
att agt gct ggg cgt atc tat ata agt gcc aat agg cag ctc tgc tac    1452
Ile Ser Ala Gly Arg Ile Tyr Ile Ser Ala Asn Arg Gln Leu Cys Tyr
    450                 455                 460 cac cac tct ttg aac tgg acc aag gtg ctt cgg ggg cct acg gaa gag    1500
His His Ser Leu Asn Trp Thr Lys Val Leu Arg Gly Pro Thr Glu Glu
465                 470                 475                 480 cga cta gac atc aag cat aat cgg ccg cgc aga gac tgc ggt gag gga    1548
Arg Leu Asp Ile Lys His Asn Arg Pro Arg Arg Asp Cys Gly Glu Gly
                485                 490                 495 aag ggt ctg cta ggt ggt gag aat agg gag tca ggg agg aga ggg ctg    1596
Lys Gly Leu Leu Gly Gly Glu Asn Arg Glu Ser Gly Arg Arg Gly Leu
            500                 505                 510 aaa gga cta ttc tgc cct aga cgt ggg agt agg gtt gag gga tgg aac    1644
Lys Gly Leu Phe Cys Pro Arg Arg Gly Ser Arg Val Glu Gly Trp Asn
        515                 520                 525 caa gga gaa ggg ggc tgt taggctggaa gcagtaacga ggaagaataa           1692
Gln Gly Glu Gly Gly Cys
    530 tgaagagagg gcttgctggg agtcctcaga ctcctctcct aacccacccc ttcctttcca  1752 gtggcagagg gcaaagtgtg tgacccactg tgctcctctg ggggatgctg gggcccaggc  1812 cctggtcagt gcttgtcctg tcgaaattat agccgaggag gtgtctgtgt gacccactgc  1872 aactttctga atgggtacag taaggggagc cagtcaagga tgggtggggg tggggccctg  1932 caatggaact gttcaggtgg catacaataa aagtctttag acagcaaaaa aaaaaaaaaa  1992 aaaaaaaaaa aaa                                                     2005

<210> SEQ ID NO 6
<211> LENGTH: 534
<212> TYPE: PRT
<213> ORGANISM: Homo sapiens

<400> SEQUENCE: 6

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
```

```
                    180                 185                 190
Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
        210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Asp Cys Gly Glu Gly
                485                 490                 495

Lys Gly Leu Leu Gly Gly Glu Asn Arg Glu Ser Gly Arg Arg Gly Leu
            500                 505                 510

Lys Gly Leu Phe Cys Pro Arg Arg Gly Ser Arg Val Glu Gly Trp Asn
        515                 520                 525

Gln Gly Glu Gly Gly Cys
    530

<210> SEQ ID NO 7
<211> LENGTH: 1320
<212> TYPE: DNA
<213> ORGANISM: Homo sapiens
<220> FEATURE:
<221> NAME/KEY: CDS
<222> LOCATION: (61)..(1260)

<400> SEQUENCE: 7
```

-continued

```
cgggcccccc ctcgaggtcg ggccggactt ggctgggctc ccttcaccct ctgcggagtc        60 atg agg gcg aac gac gct ctg cag gtc ctg ggc ttg ctt ttc agc ctg       108
Met Arg Ala Asn Asp Ala Leu Gln Val Leu Gly Leu Leu Phe Ser Leu
1               5                   10                  15 gcc cgg ggc tcc gag gtg ggc aac tct cag gca gtg tgt cct ggg act       156
Ala Arg Gly Ser Glu Val Gly Asn Ser Gln Ala Val Cys Pro Gly Thr
            20                  25                  30 ctg aat ggc ctg agt gtg acc ggc gat gct gag aac caa tac cag aca       204
Leu Asn Gly Leu Ser Val Thr Gly Asp Ala Glu Asn Gln Tyr Gln Thr
        35                  40                  45 ctg tac aag ctc tac gag agg tgt gag gtg gtg atg ggg aac ctt gag       252
Leu Tyr Lys Leu Tyr Glu Arg Cys Glu Val Val Met Gly Asn Leu Glu
    50                  55                  60 att gtg ctc acg gga cac aat gcc gac ctc tcc ttc ctg cag tgg att       300
Ile Val Leu Thr Gly His Asn Ala Asp Leu Ser Phe Leu Gln Trp Ile
65                  70                  75                  80 cga gaa gtg aca ggc tat gtc ctc gtg gcc atg aat gaa ttc tct act       348
Arg Glu Val Thr Gly Tyr Val Leu Val Ala Met Asn Glu Phe Ser Thr
                85                  90                  95 cta cca ttg ccc aac ctc cgc gtg gtg cga ggg acc cag gtc tac gat       396
Leu Pro Leu Pro Asn Leu Arg Val Val Arg Gly Thr Gln Val Tyr Asp
            100                 105                 110 ggg aag ttt gcc atc ttc gtc atg ttg aac tat aac acc aac tcc agc       444
Gly Lys Phe Ala Ile Phe Val Met Leu Asn Tyr Asn Thr Asn Ser Ser
        115                 120                 125 cac gct ctg cgc cag ctc cgc ttg act cag ctc acc gag att ctg tca       492
His Ala Leu Arg Gln Leu Arg Leu Thr Gln Leu Thr Glu Ile Leu Ser
    130                 135                 140 ggg ggt gtt tat att gag aag aac gat aag ctt tgt cac atg gac aca       540
Gly Gly Val Tyr Ile Glu Lys Asn Asp Lys Leu Cys His Met Asp Thr
145                 150                 155                 160 att gac tgg agg gac atc gtg agg gac cga gat gct gag ata gtg gtg       588
Ile Asp Trp Arg Asp Ile Val Arg Asp Arg Asp Ala Glu Ile Val Val
                165                 170                 175 aag gac aat ggc aga agc tgt ccc ccc tgt cat gag gtt tgc aag ggg       636
Lys Asp Asn Gly Arg Ser Cys Pro Pro Cys His Glu Val Cys Lys Gly
            180                 185                 190 cga tgc tgg ggt cct gga tca gaa gac tgc cag aca ttg acc aag acc       684
Arg Cys Trp Gly Pro Gly Ser Glu Asp Cys Gln Thr Leu Thr Lys Thr
        195                 200                 205 atc tgt gct cct cag tgt aat ggt cac tgc ttt ggg ccc aac ccc aac       732
Ile Cys Ala Pro Gln Cys Asn Gly His Cys Phe Gly Pro Asn Pro Asn
    210                 215                 220 cag tgc tgc cat gat gag tgt gcc ggg ggc tgc tca ggc cct cag gac       780
Gln Cys Cys His Asp Glu Cys Ala Gly Gly Cys Ser Gly Pro Gln Asp
225                 230                 235                 240 aca gac tgc ttt gcc tgc cgg cac ttc aat gac agt gga gcc tgt gta       828
Thr Asp Cys Phe Ala Cys Arg His Phe Asn Asp Ser Gly Ala Cys Val
                245                 250                 255 cct cgc tgt cca cag cct ctt gtc tac aac aag cta act ttc cag ctg       876
Pro Arg Cys Pro Gln Pro Leu Val Tyr Asn Lys Leu Thr Phe Gln Leu
            260                 265                 270 gaa ccc aat ccc cac acc aag tat cag tat gga gga gtt tgt gta gcc       924
Glu Pro Asn Pro His Thr Lys Tyr Gln Tyr Gly Gly Val Cys Val Ala
        275                 280                 285 agc tgt ccc cat aac ttt gtg gtg gat caa aca tcc tgt gtc agg gcc       972
Ser Cys Pro His Asn Phe Val Val Asp Gln Thr Ser Cys Val Arg Ala
    290                 295                 300 tgt cct cct gac aag atg gaa gta gat aaa aat ggg ctc aag atg tgt      1020
```

```
Cys Pro Pro Asp Lys Met Glu Val Asp Lys Asn Gly Leu Lys Met Cys
305                 310                 315                 320 gag cct tgt ggg gga cta tgt ccc aaa gcc tgt gag gga aca ggc tct    1068
Glu Pro Cys Gly Gly Leu Cys Pro Lys Ala Cys Glu Gly Thr Gly Ser
                325                 330                 335 ggg agc cgc ttc cag act gtg gac tcg agc aac att gat gga ttt gtg    1116
Gly Ser Arg Phe Gln Thr Val Asp Ser Ser Asn Ile Asp Gly Phe Val
            340                 345                 350 aac tgc acc aag atc ctg ggc aac ctg gac ttt ctg atc acc ggc ctc    1164
Asn Cys Thr Lys Ile Leu Gly Asn Leu Asp Phe Leu Ile Thr Gly Leu
        355                 360                 365 aat ggg tta gag atc ctg cct tcc ctc ctt aga ccc cag ccc acg cac    1212
Asn Gly Leu Glu Ile Leu Pro Ser Leu Leu Arg Pro Gln Pro Thr His
    370                 375                 380 ccc tca cag ttc att tca ttg gcc aaa act ttc cta tgt gga gct gac    1260
Pro Ser Gln Phe Ile Ser Leu Ala Lys Thr Phe Leu Cys Gly Ala Asp
385                 390                 395                 400 taggaatcaa agtcataaaa ttctagcctg ttaaaaaaaa aaaaaaaaaa aaaaaaaaaa   1320

<210> SEQ ID NO 8
<211> LENGTH: 400
<212> TYPE: PRT
<213> ORGANISM: Homo sapiens

<400> SEQUENCE: 8

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
```

-continued

```
                    245                 250                 255
Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Leu Glu Ile Leu Pro Ser Leu Leu Arg Pro Gln Pro Thr His
            370                 375                 380

Pro Ser Gln Phe Ile Ser Leu Ala Lys Thr Phe Leu Cys Gly Ala Asp
385                 390                 395                 400
```